US008835622B2

(12) United States Patent
Pinot et al.

(10) Patent No.: US 8,835,622 B2
(45) Date of Patent: Sep. 16, 2014

(54) EXPRESSION CASSETTES FOR SEED-SPECIFIC EXPRESSION IN PLANTS

(75) Inventors: Franck Pinot, Westhoffen (FR); Daniele Werck, Souffelweyersheim (FR); Jürgen Ehlting, Victoria BC, CA (US); Alexandre Olry, Nancy (FR); Peter Denolf, Velzeke (BE); Katrien Van Audenhove, Gent (BE); Lien Van de Putte, Bassevelde (BE); Esmeralda Posada, Gent (BE)

(73) Assignees: Bayer BioScience N.V., Gent (BE); Le Centre National de la Recherche Scientifique, Paris Cedex (FR)

( * ) Notice: Subject to any disclaimer, the term of this patent is extended or adjusted under 35 U.S.C. 154(b) by 386 days.

(21) Appl. No.: 13/131,307

(22) PCT Filed: Nov. 25, 2009

(86) PCT No.: PCT/EP2009/008387
§ 371 (c)(1),
(2), (4) Date: Aug. 1, 2011

(87) PCT Pub. No.: WO2010/060609
PCT Pub. Date: Jun. 3, 2010

(65) Prior Publication Data
US 2011/0296552 A1 Dec. 1, 2011

Related U.S. Application Data

(60) Provisional application No. 61/201,648, filed on Dec. 12, 2008.

(30) Foreign Application Priority Data

Nov. 26, 2008 (EP) .................................. 08356145

(51) Int. Cl.
*C07H 21/04* (2006.01)
*C12N 15/82* (2006.01)
*C12N 5/10* (2006.01)
*A01H 5/00* (2006.01)
*C12N 15/00* (2006.01)
*C07K 14/415* (2006.01)

(52) U.S. Cl.
CPC .......... *C12N 15/8234* (2013.01); *C07K 14/415* (2013.01)
USPC .......... 536/24.1; 800/278; 800/298; 435/419; 435/320.1

(58) Field of Classification Search
None
See application file for complete search history.

(56) References Cited

U.S. PATENT DOCUMENTS

| 4,757,011 | A | 7/1988 | Chaleff et al. |
|---|---|---|---|
| 4,769,061 | A | 9/1988 | Comai |
| 4,940,835 | A | 7/1990 | Shah et al. |
| 4,971,908 | A | 11/1990 | Kishore et al. |
| 5,593,874 | A | 1/1997 | Brown et al. |
| 5,641,876 | A | 6/1997 | McElroy et al. |
| 5,659,122 | A | 8/1997 | Austin |
| 2004/0034888 | A1* | 2/2004 | Liu et al. ................. 800/289 |
| 2004/0255350 | A1* | 12/2004 | Chaudhary et al. ........... 800/288 |
| 2006/0150283 | A1* | 7/2006 | Alexandrov et al. ......... 800/288 |

FOREIGN PATENT DOCUMENTS

| EP | 0255378 | 2/1988 |
|---|---|---|
| WO | 0216655 | 2/2002 |

OTHER PUBLICATIONS

Potenza__In Vitro Cell Dev Biol Plant__40__1__2004.*
Komarnytsky Genetic Engin__25__113__2003.*
Dolferus__Plant Phys__105__1075__1994.*
Donald__EMBO J__9__1717__1990.*
Kim__Plant Mol Biol__24__105__1994.*
Tsang__ES905808__2007.*
Rounsley__AC002388__2002.*
Rounsley__AAC31835__2002.*
Schmid__Nature Genet__37__501__2005.*
Winter__PLoS ONE__2__e718__2007.*
Li__Genomics 86__718__2005.*
Bak, Soren et al., "Transgenic Tobacco and *Arabidopsis* Plants Expressing the Two Multifunctional *Sorghum* Cytochrome P450 Enzymes, CYP79A1 and CYP71E1, are Cyanogenic and Accumulate Metobolites Derived from Intermediates in Dhurrin Biosynthesis", Plant Physiology, Aug. 2000, vol. 123, pp. 1437-1448.
Barta, Endre et al., "DoOP: Databases of Orthologous Promoters, collections of clusters of orthologous upstream sequences from chordates and plants", Nucleic Acids Research, 2005, vol. 33, pp. D86-D90.
Baumlein, Helmut et al., "A novel seed protein gene from *Vicia faba* is developmentally regulated in transgenic tobacco and *Arabidopsis* plants", Mol Gen Genet, 1991, vol. 225, pp. 459-467.
Cardini, G. et al., "The Enzymatic Hydroxylation of n-Octane by *Corynebacterium* sp. Strain 7E1C", The Journal of Biological Chemistry, 1970, vol. 245, No. 11, pp. 2789-2796.
Clough, Steven et al., "Floral dip: a simplified method for Agrobacterium-mediated transformation of *Arabidopsis thaliana*", The Plant Journal, 1998, vol. 16, No. 6, pp. 735-743.
Ehlting, Jurgen et al., "An extensive (co-)expression analysis tool for the cytochrome P450 superfamily in *Arabidopsis thaliana*", BMC Plant Biology, 2008, vol. 8, No. 47, 19 pgs.
Fisher, Michael B. et al., "Positional Specificity of Rabbit CYP4B1 for w-Hydroxylation of Short-Medium Chain Fatty Acids and Hydrocarbons", Biochemical & Biophysical Research Communications, 1998, vol. 248, pp. 352-355.
Funhoff, Enrico G. et al., "CYP153A6, a Soluble P450 Oxygenase Catalyzing Terminal-Alkane Hydroxylation", Journal of Bacteriology, 2006, vol. 188, No. 14, pp. 5220-5227.

(Continued)

*Primary Examiner* — Medina A Ibrahim
*Assistant Examiner* — Russell Boggs

(57) ABSTRACT

The present invention relates to materials and methods for the expression of a gene of interest specifically in seeds of plants, even more specifically in oilseed plants. In particular, the invention provides an expression cassette for regulating seed-specific expression in plants.

11 Claims, 3 Drawing Sheets

(56) References Cited

OTHER PUBLICATIONS

Galbiati, Massimo et al., "Large-scale T-DNA mutagenesis in *Arabidopsis* for functional genomic analysis", Funct Integr Genomics, 2000, 1:25-34.

Hofer, Rene, 2008, Mathematisch-Naturwissenschftlische Fakultat der Reinischen Friedrich-Wilhem-Universitat Bon, p. 34, table 9.

Jefferson, Richard A. et al., "GUS fusions: B-glucuronidase as a sensitive and versatile gene fusion marker in higher plants", The EMBO Journal, 1987, vol. 6, No. 13, pp. 3901-3907.

Omura, Tsuneo et al., "The Carbon Monoxide-binding Pigment of Liver Microsomes", The Journal of Biological Chemistry, 1964, vol. 239, No. 7, pp. 2370-2378.

Pearson, William et al., "Improved tools for biological sequence comparison", Proc. Natl. Acad. Sci., 1988, vol. 85, pp. 2444-2448.

Pompon, D. et al., "Yeast Expression of Animal and Plant P450s in Optimized Redox Environments", Methods in Enzymology, vol. 272, pp. 51-64.

Scheller, Ulrich et al., "Characterization of the n-Alkane and Fatty Acid Hydroxylating Cytochrome P450 Forms 52A3 and 52A4", Archives of Biochemistry and Biophysics, 1996, vol. 328, No. 2, pp. 245-254.

Schuler, Mary A. et al., "Functional Genomics of P450s", Annual Review of Plant Physiology and Plant Molecular Biology, vol. 54, pp. 629-6446.

International Search Report for PCT/EP2009/008387.

\* cited by examiner

SEQUENCE LISTING

```
<160> NUMBER OF SEQ ID NOS: 31

<210> SEQ ID NO 1
<211> LENGTH: 1210
<212> TYPE: DNA
<213> ORGANISM: Arabidopsis thaliana

<400> SEQUENCE: 1
ggtgctgttt cttctatctc ctatcttgtt catcgttcct ttttggctct gatcatttct     60
tgtgccaaga tctattgacg atattaccct ccgctctgtt attcccttag ataaatcata    120
tgtgttgtaa attaggccca atgacatgct catgaaaatg gaaaactaaa cagagcttct    180
gtcacttgac gtttcaggtt ttcaaaagag aaacattaat acagagcgga gggtaatttt    240
gtgtcgattc atatttttca cagagcaaaa agtttccttc agcaagaatc aattcatatc    300
agaaatacag ataataatga gaaaacacca tttttgaaga agccgataca taagttgaa     360 taaatcaatt cgatttcatt tgtcaagaac cggaactgga cccatatcaa accggtttta    420
ttgatcttcc tttgtctttc cgagagcatg gggagtgcag aaaatgatga catggacata    480
gagtgagcaa aggagataat atctactaca tagcaatgtg taggatgact tacatttagg    540
gtcaagatga ggaagatttc aagccagaga gatggcttaa ggatggcgtg ttccaacctt    600
aagaaataca tttctaataa aacctgagat gttttctttc tttgactatg tatgtaggct    660
ggtccaagaa tctgtcttgg caaagatttc gcataccggc aaatgaagac acttattcac    720
ttctttcgct tcaaaatggc tgatgagaag actactgtat gttactagag aatgcttact    780
cttcgtgtcc aaggaggaca aacacctcta aaaaactttt ttttcatatc aaataatata    840
tggaagtata atcaattaaa aaaaacacat ttttccccca tatcttctgt tttgtcttta    900
tataatttga ttacgtggta caaagaaag ttgaggccct aattcatatt gtgcgacttt     960
ttcacccaca attactacat gagaaaacat caaaacgaca aaatcggtta cactcaacgt   1020
taaccttcga ggtaaaagag agggttcaga atgtttcgtt ggatgcgtgt aaaatccgtc   1080
ttgacttttc gtgattgttg aatcgtctat atatgacttc ttagcgggaa gattgaaaaa   1140
atcagacaac aagacgaaac aacttccaag ccaaaaaaaa aaaagtgaat caatggagat   1200
tttgacgagc                                                         1210

<210> SEQ ID NO 2
<211> LENGTH: 920
<212> TYPE: DNA
<213> ORGANISM: Arabidopsis thaliana

<400> SEQUENCE: 2
aagcttgcaa tctctcagat acttgatttt gccaatttga aatcttctct cggtacgatc      60
```

-continued

```
tcaccttctc cttttcacta ccatatcatt caacaaatca tcatcactac aactttattt      120
ttcaacataa catatataag tcaaaacaaa cttatcaaaa cctggaacta atatacgaag      180
gagaaggagt agaagtagct tcattcatga tcctttgagc atttctataa tgaagaagag      240
catcatcatg taaaccccac tcttctgctc taaccccttt agcgattttcc tctttcgcta     300 aatcgaagta tcctttaagc ttatacgcaa ttcgttcgtt agtaaccgga actccatcga     360
taccattcat ggactcagaa gaagttgatg atgatgaaac actaggatct ttcttagatt      420
cttcgttgag aatagagcta acgaatcaa ttatacctct gaggaaactc atatctaagc       480
aataaacaat aaaatcgatc atcacttccg agtttaatca acaaaaaac aaaaaaacat      540 caagaaggca aaattggttt cacgcaccat gttgtgctcg tatatataac tcatgtcgag      600
aagattcgaa tcaaaatcga aatcaaatcc agcgaattga agaaatttga tgaaatctta     660
tgaactggga aatacgcaaa cgatgaacaa accaaacaac acacggtcaa gtctttaacc     720
ctctacgtag aaagaaggtt ctaatgggct ttacaaggcc tatacatata taatcttagg     780
cccaatgata ttttatcggt ggcccagttt tgttttgttt tcgatcatct tcttcgccgt     840
taaatatttt attctctacg gtaccttttg tctctttgta ctttcagata ctatcgttga     900
cttcgaagta agaaaagaaa                                                 920
```

<210> SEQ ID NO 3
<211> LENGTH: 1775
<212> TYPE: DNA
<213> ORGANISM: Arabidopsis thaliana
<220> FEATURE:
<221> NAME/KEY: CDS
<222> LOCATION: (12)..(1544)

<400> SEQUENCE: 3

```
aagaaaagaa a atg gag att ttg acg agc ata gct att aca gta gca aca      50
            Met Glu Ile Leu Thr Ser Ile Ala Ile Thr Val Ala Thr
              1               5                  10 acg atc ttc atc gtt ttg tgt ttc act atc tat ctt atg atc aga atc      98
Thr Ile Phe Ile Val Leu Cys Phe Thr Ile Tyr Leu Met Ile Arg Ile
     15                  20                  25 ttt acc ggg aaa tca aga aac gac aag aga tat gct cca gtg cat gcc     146
Phe Thr Gly Lys Ser Arg Asn Asp Lys Arg Tyr Ala Pro Val His Ala
 30              35                  40                  45 acg gtc ttt gat ctt ctc ttc cac agc gac gag tta tac gat tac gag     194
Thr Val Phe Asp Leu Leu Phe His Ser Asp Glu Leu Tyr Asp Tyr Glu
             50                  55                  60 aca gag atc gcg aga gag aag ccg act tac agg ttt ttg agt cca gga     242
Thr Glu Ile Ala Arg Glu Lys Pro Thr Tyr Arg Phe Leu Ser Pro Gly
         65                  70                  75 cag agc gag ata tta act gca gat cct cgt aac gtg gag cat att ctc     290
Gln Ser Glu Ile Leu Thr Ala Asp Pro Arg Asn Val Glu His Ile Leu
     80                  85                  90 aag aca aga ttc gat aac tat agt aaa gga cac agt agt aga gag aat     338
Lys Thr Arg Phe Asp Asn Tyr Ser Lys Gly His Ser Ser Arg Glu Asn
 95                 100                 105 atg gcg gat ctt cta gga cat ggg atc ttt gct gtt gat gga gag aaa     386
Met Ala Asp Leu Leu Gly His Gly Ile Phe Ala Val Asp Gly Glu Lys
110                 115                 120                 125 tgg aga caa cag agg aag ctt tcg agc ttt gag ttc tct act aga gtt     434
Trp Arg Gln Gln Arg Lys Leu Ser Ser Phe Glu Phe Ser Thr Arg Val
                130                 135                 140 tta aga gat ttt agc tgc tct gtt ttt agg aga aat gca tct aag ctt     482
```

```
                Leu Arg Asp Phe Ser Cys Ser Val Phe Arg Arg Asn Ala Ser Lys Leu
                                145                 150                 155 gtt ggt ttt gtc tcg gag ttt gct ctc tct gga aaa gct ttt gat gct         530
Val Gly Phe Val Ser Glu Phe Ala Leu Ser Gly Lys Ala Phe Asp Ala
            160                 165                 170 caa gat ttg ttg atg aga tgt aca ctg gac tcc atc ttt aaa gtt ggg         578
Gln Asp Leu Leu Met Arg Cys Thr Leu Asp Ser Ile Phe Lys Val Gly
175                 180                 185 ttt ggt gtg gag tta aaa tgt ttg gat ggg ttt agc aaa gaa ggg caa         626
Phe Gly Val Glu Leu Lys Cys Leu Asp Gly Phe Ser Lys Glu Gly Gln
190                 195                 200                 205 gag ttt atg gaa gct ttt gat gaa ggt aac gtt gca act agt tcc aga         674
Glu Phe Met Glu Ala Phe Asp Glu Gly Asn Val Ala Thr Ser Ser Arg
                210                 215                 220 ttc atc gat cct ctt tgg aag ctg aaa tgg ttt ttc aac att gga tca         722
Phe Ile Asp Pro Leu Trp Lys Leu Lys Trp Phe Phe Asn Ile Gly Ser
                225                 230                 235 caa tct aag ctc aag aag agc att gct act ata gat aaa ttt gtc tat         770
Gln Ser Lys Leu Lys Lys Ser Ile Ala Thr Ile Asp Lys Phe Val Tyr
            240                 245                 250 agt ctc att acc act aaa agg aaa gag ctt gct aag gaa cag aac act         818
Ser Leu Ile Thr Thr Lys Arg Lys Glu Leu Ala Lys Glu Gln Asn Thr
255                 260                 265 gtt gtt aga gag gac ata cta tcg aga ttc cta gtg gag agt gag aaa         866
Val Val Arg Glu Asp Ile Leu Ser Arg Phe Leu Val Glu Ser Glu Lys
270                 275                 280                 285 gat ccg gag aac atg aat gat aag tac ctg agg gat ata att ctg aac         914
Asp Pro Glu Asn Met Asn Asp Lys Tyr Leu Arg Asp Ile Ile Leu Asn
                290                 295                 300 ttc atg att gct ggt aag gac aca acc gct gca cta ctc tct tgg ttc         962
Phe Met Ile Ala Gly Lys Asp Thr Thr Ala Ala Leu Leu Ser Trp Phe
                305                 310                 315 ttg tac atg ctc tgc aaa aac cca ctt gtt cag gag aaa atc gta caa        1010
Leu Tyr Met Leu Cys Lys Asn Pro Leu Val Gln Glu Lys Ile Val Gln
            320                 325                 330 gaa atc aga gat gtg aca ttt agt cac gag aaa acg acc gat gta aat        1058
Glu Ile Arg Asp Val Thr Phe Ser His Glu Lys Thr Thr Asp Val Asn
335                 340                 345 ggt ttc gtt gaa agt att aac gaa gag gct ctt gat gag atg cac tac        1106
Gly Phe Val Glu Ser Ile Asn Glu Glu Ala Leu Asp Glu Met His Tyr
350                 355                 360                 365 ctc cat gca gcc ttg tct gag acc ttg agg ctc tac cct cct gtg cct        1154
Leu His Ala Ala Leu Ser Glu Thr Leu Arg Leu Tyr Pro Pro Val Pro
                370                 375                 380 gtg gac atg agg tgt gca gaa aat gat gac gtt ctt cca gat gga cat        1202
Val Asp Met Arg Cys Ala Glu Asn Asp Asp Val Leu Pro Asp Gly His
                385                 390                 395 aga gtg agc aaa ggg gat aat atc tac tac ata gcc tat gca atg ggt        1250
Arg Val Ser Lys Gly Asp Asn Ile Tyr Tyr Ile Ala Tyr Ala Met Gly
            400                 405                 410 agg atg act tac att tgg ggt caa gat gct gaa gaa ttc aag cca gag        1298
Arg Met Thr Tyr Ile Trp Gly Gln Asp Ala Glu Glu Phe Lys Pro Glu
415                 420                 425 aga tgg ctc aag gac ggc tta ttc caa ccc gaa tca cca ttc aaa ttc        1346
Arg Trp Leu Lys Asp Gly Leu Phe Gln Pro Glu Ser Pro Phe Lys Phe
430                 435                 440                 445 ata agc ttt cat gct ggt cca aga atc tgt ctt ggc aag gat ttc gca        1394
Ile Ser Phe His Ala Gly Pro Arg Ile Cys Leu Gly Lys Asp Phe Ala
                450                 455                 460
```

```
tac cgg cag atg aag ata gta tca atg gca ctt ctt cac ttc ttt cgc     1442
Tyr Arg Gln Met Lys Ile Val Ser Met Ala Leu Leu His Phe Phe Arg
            465                 470                 475 ttc aaa atg gct gat gag aac agc aag gtg tat tac aag aga atg ctt     1490
Phe Lys Met Ala Asp Glu Asn Ser Lys Val Tyr Tyr Lys Arg Met Leu
            480                 485                 490 act ctt cat gtc gat gga gga ctc cat ctc tgt gca atc ccg agg aca     1538
Thr Leu His Val Asp Gly Gly Leu His Leu Cys Ala Ile Pro Arg Thr
            495                 500                 505 agc act tgagtactta accagaatac tttccatact tttatagtgc ctccatgagt      1594
Ser Thr
510 tttggtaaca ttctcaataa aggtggaaca agacaccaat aacgttccat gtaataaata   1654 atctgccttt atagatcttg ggatgactca actatcacat atattagaat ccgatgaaca   1714 cgacacgata ttgtataatt ttacagtcac ctagtacaat aaagcagata agtcgcactg   1774 t                                                                   1775

<210> SEQ ID NO 4
<211> LENGTH: 511
<212> TYPE: PRT
<213> ORGANISM: Arabidopsis thaliana

<400> SEQUENCE: 4

Met Glu Ile Leu Thr Ser Ile Ala Ile Thr Val Ala Thr Thr Ile Phe
1               5                   10                  15

Ile Val Leu Cys Phe Thr Ile Tyr Leu Met Ile Arg Ile Phe Thr Gly
            20                  25                  30

Lys Ser Arg Asn Asp Lys Arg Tyr Ala Pro Val His Ala Thr Val Phe
        35                  40                  45

Asp Leu Leu Phe His Ser Asp Glu Leu Tyr Asp Tyr Glu Thr Glu Ile
    50                  55                  60

Ala Arg Glu Lys Pro Thr Tyr Arg Phe Leu Ser Pro Gly Gln Ser Glu
65                  70                  75                  80

Ile Leu Thr Ala Asp Pro Arg Asn Val Glu His Ile Leu Lys Thr Arg
                85                  90                  95

Phe Asp Asn Tyr Ser Lys Gly His Ser Ser Arg Glu Asn Met Ala Asp
            100                 105                 110

Leu Leu Gly His Gly Ile Phe Ala Val Asp Gly Glu Lys Trp Arg Gln
        115                 120                 125

Gln Arg Lys Leu Ser Ser Phe Glu Phe Ser Thr Arg Val Leu Arg Asp
    130                 135                 140

Phe Ser Cys Ser Val Phe Arg Arg Asn Ala Ser Lys Leu Val Gly Phe
145                 150                 155                 160

Val Ser Glu Phe Ala Leu Ser Gly Lys Ala Phe Asp Ala Gln Asp Leu
                165                 170                 175

Leu Met Arg Cys Thr Leu Asp Ser Ile Phe Lys Val Gly Phe Gly Val
            180                 185                 190

Glu Leu Lys Cys Leu Asp Gly Phe Ser Lys Glu Gly Gln Glu Phe Met
        195                 200                 205

Glu Ala Phe Asp Glu Gly Asn Val Ala Thr Ser Arg Phe Ile Asp
    210                 215                 220

Pro Leu Trp Lys Leu Lys Trp Phe Phe Asn Ile Gly Ser Gln Ser Lys
225                 230                 235                 240

Leu Lys Lys Ser Ile Ala Thr Ile Asp Lys Phe Val Tyr Ser Leu Ile
                245                 250                 255
```

-continued

Thr Thr Lys Arg Lys Glu Leu Ala Lys Glu Gln Asn Thr Val Val Arg
            260                 265                 270

Glu Asp Ile Leu Ser Arg Phe Leu Val Glu Ser Lys Asp Pro Glu
        275                 280                 285

Asn Met Asn Asp Lys Tyr Leu Arg Asp Ile Ile Leu Asn Phe Met Ile
290                 295                 300

Ala Gly Lys Asp Thr Thr Ala Ala Leu Leu Ser Trp Phe Leu Tyr Met
305                 310                 315                 320

Leu Cys Lys Asn Pro Leu Val Gln Glu Lys Ile Val Gln Glu Ile Arg
                325                 330                 335

Asp Val Thr Phe Ser His Glu Lys Thr Thr Asp Val Asn Gly Phe Val
            340                 345                 350

Glu Ser Ile Asn Glu Glu Ala Leu Asp Glu Met His Tyr Leu His Ala
        355                 360                 365

Ala Leu Ser Glu Thr Leu Arg Leu Tyr Pro Pro Val Pro Val Asp Met
370                 375                 380

Arg Cys Ala Glu Asn Asp Val Leu Pro Asp Gly His Arg Val Ser
385                 390                 395                 400

Lys Gly Asp Asn Ile Tyr Tyr Ile Ala Tyr Ala Met Gly Arg Met Thr
                405                 410                 415

Tyr Ile Trp Gly Gln Asp Ala Glu Glu Phe Lys Pro Glu Arg Trp Leu
            420                 425                 430

Lys Asp Gly Leu Phe Gln Pro Glu Ser Pro Phe Lys Phe Ile Ser Phe
        435                 440                 445

His Ala Gly Pro Arg Ile Cys Leu Gly Lys Asp Phe Ala Tyr Arg Gln
450                 455                 460

Met Lys Ile Val Ser Met Ala Leu Leu His Phe Phe Arg Phe Lys Met
465                 470                 475                 480

Ala Asp Glu Asn Ser Lys Val Tyr Tyr Lys Arg Met Leu Thr Leu His
                485                 490                 495

Val Asp Gly Gly Leu His Leu Cys Ala Ile Pro Arg Thr Ser Thr
            500                 505                 510

```
<210> SEQ ID NO 5
<211> LENGTH: 24
<212> TYPE: DNA
<213> ORGANISM: artificial primer
<220> FEATURE:
<223> OTHER INFORMATION: PCR primer

<400> SEQUENCE: 5
ggtatactcc tgtacacgcc acaa                                          24

<210> SEQ ID NO 6
<211> LENGTH: 22
<212> TYPE: DNA
<213> ORGANISM: artificial primer
<220> FEATURE:
<223> OTHER INFORMATION: PCR primer

<400> SEQUENCE: 6
cctgaaagta ggctttgtcc tc                                            22

<210> SEQ ID NO 7
<211> LENGTH: 21
<212> TYPE: DNA
<213> ORGANISM: artificial primer
<220> FEATURE:
```

```
<223> OTHER INFORMATION: PCR primer

<400> SEQUENCE: 7
cagtagtaga gagaatatgg c                                              21

<210> SEQ ID NO 8
<211> LENGTH: 21
<212> TYPE: DNA
<213> ORGANISM: artificial primer
<220> FEATURE:
<223> OTHER INFORMATION: PCR primer

<400> SEQUENCE: 8
ctctagtaga gaactcaaag c                                              21

<210> SEQ ID NO 9
<211> LENGTH: 23
<212> TYPE: DNA
<213> ORGANISM: artificial primer
<220> FEATURE:
<223> OTHER INFORMATION: PCR primer

<400> SEQUENCE: 9
atggagattt tgacgagcat agc                                            23

<210> SEQ ID NO 10
<211> LENGTH: 28
<212> TYPE: DNA
<213> ORGANISM: artificial primer
<220> FEATURE:
<223> OTHER INFORMATION: PCR primer

<400> SEQUENCE: 10
cataagatag atagtgaaac acaaaacg                                       28

<210> SEQ ID NO 11
<211> LENGTH: 33
<212> TYPE: DNA
<213> ORGANISM: artificial primer
<220> FEATURE:
<223> OTHER INFORMATION: PCR primer

<400> SEQUENCE: 11
cgaagcttaa gcttgcaatc tctcagatac ttg                                 33

<210> SEQ ID NO 12
<211> LENGTH: 30
<212> TYPE: DNA
<213> ORGANISM: artificial primer
<220> FEATURE:
<223> OTHER INFORMATION: PCR primer

<400> SEQUENCE: 12
gggatccact tcgaagtcaa cgatagtatc                                     30

<210> SEQ ID NO 13
<211> LENGTH: 1953
<212> TYPE: DNA
<213> ORGANISM: Brassica napus

<400> SEQUENCE: 13
ttgatgtcag aaacaaagca aaatgtgaac tcacttgtgc attaataaaa aaatcacctg     60
cacgtttacc aagagcttgc aacctctcag atacttgact ttgccattta gaaatcttct    120
ctctataaga tctcaccttc tccttctcac ttaccatata cacaagtcaa caccacaaat    180
```

```
aaaaaccaat gttcaagaaa ctatacaaga gtagattaat tatacattta tataaaatat    240
tttagttgtt aggtttaatt ataaattatt atgctgagtt agttatatac aaaacaaaat    300
aaattagaaa aatttgtgaa tttgaacaaa acattattgc ttaatttaac aaaattagac    360
taatttagat cagattttaa ggaaaatgtt tagtataaat ctgaaagaac attacttgga    420
actgatgtaa aaggagaag gcgtggaggt agcttcactc atgatcctct gggcgtttct     480
gtaatgaaga agcgcgtcgt catgtaaacc ccactcttct gctctaacac ctttggcgat    540
ctcctctttc gccaaatcga agtatccttt gagcttatac gcgacacgtt cgttactaac    600
cggagctcca tcgataacgt tcatggagga ggcagatgaa aagaagatg atacggtagg     660 atcgtgatta gattctacgg tgaagattga gctacacgaa tcaattatat ctctgaagaa    720
actcatatct aaacaaaaaa aaaacaaaga ttccgaattt aattgaacag tggtaataca    780
tgaatacaaa atcgaaaatg acagaacagg tttcacgcac catgttttgg tcggatgaat    840
tcatgtcgga gaggaatcaa tcaaatcgaa tcagaattac cagtgaatta aaaataatcg    900
aaggttgaat aatattcagt ttataagcct ctatgtcgga agaaggtttt ccaactaata    960
tcagaagccc ttggttttgg gccttttaga gtgaagatca aattgaatac cattcatgcc   1020
tatatatatc cctatagaag aaagaaggtt cgaactcgtt tcatcctgcc tactagtacc   1080
agtactgggc attcggtatt cggttccgtt ccgagtgtat cggataaatc attctaccca   1140
ataagtattt attaaatttc ggtttggttt cgattcagtt ttgatttggt atcaattcga   1200
tttcgagtaa cagtttaata tatgaatcaa atatatatac atataaaata tgtaactaat   1260
ctaagtagta tattggttat acacttacat attcgttcga gttattaaag tgctaatttg   1320 taagtatttta ctatattata atataaaata ccaaatatat atatgtataa tataagagaa  1380
tacaatttac taccttatat tagaaagttg aaatttgttt ttcttttcga atatttgagt   1440
gtatattcgg ttcccggttc tggtttcggt tcggttaatc ggatgtaaaa aaatatgaac   1500
cattcgagta tctgaaggtt tcggtttcca aataattcag ttccgttccg gttaagtttt   1560
tcggttttgg tttttttggc ccaaggctac tgcctacatt ttaatacgat tcttaattt    1620 aggccttaaa tagaggaatc atatcaaaca aaaaatttca gtaaattaaa aattaatgac   1680
atcgagtgaa tgagctggaa aaaaaaagaa aaaaactctc ttcttcttct tttgaaacac   1740
cacgaagaaa actcaaaaag ttgaatataa tctatattca taagttaata accctctaac   1800
taggtgacat ttgttttaaa atgggcctta catatttggc ctagttagat catcttcatc   1860
atggcgccgt gacatttgtt ttctacctac tgctgttgac ttctcaacgg aaagactaaa   1920
acagagaaga tctccacagc agaaacaaaa aaa                                1953

<210> SEQ ID NO 14
<211> LENGTH: 3135
<212> TYPE: DNA
<213> ORGANISM: Brassica napus

<400> SEQUENCE: 14
aaaagaaagt aaacagaaca aggctaagca cagacccatt tagatgtcaa tgaagatgct     60
gagacgttga agaatgttgc ctgtgactcg gaagcaactg ccttggcaag cattgttttt    120
ccattgccag gtggcccaaa gagaagcaaa cctaacataa agaagaactt tcaattaagt    180
aagtcacagg agaagaacaa gaagaaacca atcttacctc tagctggtct tcggagacca    240
gtgaacaaat ctcttcgttt cgctggtaaa ataaccatct ccagtaaagc ttgtttggct    300
```

-continued

```
ccatcaagtc cagctgcaag atagttcagg cataagtgtg aatcacactg atatagctca    360
taaacaatgg cactaactca ccaacatcat cccacttcac agatgggctt ctgtccacta    420
ttgttgtgtt gatcatctct tctaacttat catcgtaccc attcccagat tctttcgcag    480
gttttgggtt tgtagtagta gcatctctag ggctcctcgc cttcccaact ccacctctgg    540
gaagtgaagt cctttgtgtt gaaactcttc tattagacgc cgttgaggaa gctgaagctg    600
aagaaggaga tgatggtaca gttctctaca taatcaagaa ttcaaaaaaa gatgattcat    660
catatgaatc aatccccact acaaacatca cattctccta aagacaaata ccttattctc    720
agacactcca acacctaaaa caagaacgcc attgatgtca gaaacaaagc aaaccaatca    780
agtgtcaatg tgaactcact ggtgcattaa taaaaaaatc acctgcacgc ttaccaagag    840
cttgcaacct ctcagatact tgactttgcc atttagaaat cttctctctg taagatctca    900
ccttctcctt ctcactatac catatacaca agtcaacacc acaaataaaa accagtgttc    960
caagaaatta tacaagagta gattaattat acatttatat aatatatttt agttggtagg   1020
tttaattata aattattatg atgaaaatta tcagatttag atatacaaaa caaaataaat   1080
tagacaaatt tgtgaatttg aacaaacatt actgcttaat ttaacaaaat tagactaatt   1140
tagatcaatt ttaaattact gagagaacat tacttggaac tgatgtaaga aggagaagga   1200
gtggaggtag cttcgttcat gatcctctga gcgtttctgt aatgaagaag cgcgtcgttg   1260
tgtaaacccc actcctctgc tctaacacct ttggcgatct cctctttcgc caaatcgaag   1320
tatcctttga gcttatacgc aactcgttcg ttactaaccg gaactccatc gataacgttc   1380
atggaggagc cagatgaaga agatgatgat acggtatgat cgtgattaga ttcttccgtg   1440
aagattgagc taaacgaatc cgattatatc tctgaagaaa ctcatttcta acaaaaaaaa   1500
acaaagattc cgaatttaat tgaacagtgg tgatactcaa aatcaaaaac gacagaacag   1560
gtttcacgca ccatgaattg gtcggatgaa ttcatgtcgg agaggaatca aatcgaatca   1620
gaaataatcc aagtgactgg aaacgaagaa aaagaaaaga cgcaaggttg aataatattc   1680
atagtttata agcctctagg tcggaaagag ggtttccaac tgatatcaga aggccttggt   1740
tttgggcctt cgagagaggg atcaaattgg tttggttcgg ttccggataa gaaccattcg   1800
gtttcgagta tatcggataa atcattctta tacccaatag gtacttatga aatttcgatc   1860
cggtttcgat tcagttttg atttggtttc gatcacttac atattcgtca atccaaccat   1920
agttcgagtt actaaaatgc taatttgtaa gtatttacta tattttaata tacaatatat   1980
atatatatat atatatatat atatatatat atatatatat ataaataata taagagagta   2040
caatttacta tcctatatcc atgttcaaaa ttttgctagg cgctacgcgt gcggttgatc   2100
tgggcctagc gccgaatcaa ttaatcggag attaatcgac gattaatcgg agattagttt   2160
tctattattt tatttacata tatgcacata tattaaataa ttacaacata aacgtaaatc   2220
ttagttggta cagtggtata cccatatgta ttaaaagttc ccaacgtggg ttcgaagccc   2280
atcttttgat ttttttgctt taaatcgttt tttgtttaat gagttggaaa ttaccaattt   2340 accccgtct tttacctttt taacctgcga atttcagacc taattttcag cgttaatgtc   2400 attttcatt gattatcatt gttcttcttt gctattcacg tagctttcaa tcacttatga   2460
tagatcaatc actaaacatt cgattttgaa cactgaaaat tcaaaaaagg tggagctccg   2520 agttttggc cgaatatacc aaaatcgccg cggctactca ccggatagcg tctttccgcc   2580
gcgtactcgg ccgcctgagc cgcgttttcg aacacggccc tatattagaa agttgaaatt   2640 tgttttttg gatatttgag tacatgttcg gttttcggtt cggttaatca tatataaaaa   2700
```

```
tataggaacc atcgtgtatt tgtgggtttc gatctagatc ttgtttccgg ataattcggt    2760
tcggtttttc ggtttcggtt ttttactgc ctacatttta atatgattct taattttagg    2820
cctatttctt aaacagagga atcatatcaa acaaaaaaat tcagtaaatt aaaaattaat   2880
gacatcgagt gaatcaactg gaaaagaaga aaactctctt cttcttttt ggaacaccac    2940 gaagaaaacc caaaagttga atatcatcta ttcatatgtt aatataaacc ctctaactag   3000
gtgacatttg tttataatgg gccttaatat tcggcctaat tagatcatct tcatcatggc   3060
gccgtgacat ttgtttttcta cctactgcgg ttgacttctc aacagaaaga ctaaaaacag   3120
agaaaatctc aaaaa                                                     3135
```

<210> SEQ ID NO 15
<211> LENGTH: 15
<212> TYPE: DNA
<213> ORGANISM: artificial sequence
<220> FEATURE:
<223> OTHER INFORMATION: motif m1

<400> SEQUENCE: 15
ctctcagata cttga                                                     15

<210> SEQ ID NO 16
<211> LENGTH: 13
<212> TYPE: DNA
<213> ORGANISM: artificial sequence
<220> FEATURE:
<223> OTHER INFORMATION: motif m3

<400> SEQUENCE: 16
gaaatcttct ctc                                                       13

<210> SEQ ID NO 17
<211> LENGTH: 17
<212> TYPE: DNA
<213> ORGANISM: artificial sequence
<220> FEATURE:
<223> OTHER INFORMATION: motif m4

<400> SEQUENCE: 17
gatctcacct tctcctt                                                   17

<210> SEQ ID NO 18
<211> LENGTH: 10
<212> TYPE: DNA
<213> ORGANISM: artificial sequence
<220> FEATURE:
<223> OTHER INFORMATION: motif m7

<400> SEQUENCE: 18
tcatgatcct                                                           10

<210> SEQ ID NO 19
<211> LENGTH: 11
<212> TYPE: DNA
<213> ORGANISM: artificial sequence
<220> FEATURE:
<223> OTHER INFORMATION: motif m9

<400> SEQUENCE: 19
taatgaagaa g                                                         11

<210> SEQ ID NO 20

```
<211> LENGTH: 29
<212> TYPE: DNA
<213> ORGANISM: artificial sequence
<220> FEATURE:
<223> OTHER INFORMATION: motif m10

<400> SEQUENCE: 20
tcatgtaaac cccactcttc tgctctaac                                           29

<210> SEQ ID NO 21
<211> LENGTH: 11
<212> TYPE: DNA
<213> ORGANISM: artificial sequence
<220> FEATURE:
<223> OTHER INFORMATION: motif m13

<400> SEQUENCE: 21
tcctctttcg c                                                              11

<210> SEQ ID NO 22
<211> LENGTH: 17
<212> TYPE: DNA
<213> ORGANISM: artificial sequence
<220> FEATURE:
<223> OTHER INFORMATION: motif m14

<400> SEQUENCE: 22
aaatcgaagt atccttt                                                        17

<210> SEQ ID NO 23
<211> LENGTH: 11
<212> TYPE: DNA
<213> ORGANISM: artificial sequence
<220> FEATURE:
<223> OTHER INFORMATION: motif m15

<400> SEQUENCE: 23
agcttatacg c                                                              11

<210> SEQ ID NO 24
<211> LENGTH: 11
<212> TYPE: DNA
<213> ORGANISM: artificial sequence
<220> FEATURE:
<223> OTHER INFORMATION: motif m18

<400> SEQUENCE: 24
ctccatcgat a                                                              11

<210> SEQ ID NO 25
<211> LENGTH: 28
<212> TYPE: DNA
<213> ORGANISM: artificial sequence
<220> FEATURE:
<223> OTHER INFORMATION: motif m23

<400> SEQUENCE: 25
gagctaaacg aatcaattat acctctga                                            28

<210> SEQ ID NO 26
<211> LENGTH: 14
<212> TYPE: DNA
<213> ORGANISM: artificial sequence
<220> FEATURE:
<223> OTHER INFORMATION: motif m24

<400> SEQUENCE: 26
```

```
gaaactcata tcta                                                        14

<210> SEQ ID NO 27
<211> LENGTH: 10
<212> TYPE: DNA
<213> ORGANISM: artificial sequence
<220> FEATURE:
<223> OTHER INFORMATION: motif m25

<400> SEQUENCE: 27
aaaaaacaaa                                                             10

<210> SEQ ID NO 28
<211> LENGTH: 18
<212> TYPE: DNA
<213> ORGANISM: artificial sequence
<220> FEATURE:
<223> OTHER INFORMATION: motif m26

<400> SEQUENCE: 28
ggtttcacgc accatgtt                                                    18

<210> SEQ ID NO 29
<211> LENGTH: 13
<212> TYPE: DNA
<213> ORGANISM: artificial sequence
<220> FEATURE:
<223> OTHER INFORMATION: motif m27

<400> SEQUENCE: 29
agaaagaagg ttc                                                         13

<210> SEQ ID NO 30
<211> LENGTH: 10
<212> TYPE: DNA
<213> ORGANISM: artificial sequence
<220> FEATURE:
<223> OTHER INFORMATION: motif m28

<400> SEQUENCE: 30
tatacatata                                                             10

<210> SEQ ID NO 31
<211> LENGTH: 10
<212> TYPE: DNA
<213> ORGANISM: artificial sequence
<220> FEATURE:
<223> OTHER INFORMATION: motif m29

<400> SEQUENCE: 31
gatcatcttc                                                             10
```

EXPRESSION CASSETTES FOR SEED-SPECIFIC EXPRESSION IN PLANTS

CROSS-REFERENCE TO RELATED APPLICATIONS

This application is a §371 U.S. National Stage of International Application No. PCT/EP09/008387, filed Nov. 25, 2009, which claims the benefit of European Patent Application Serial No. 08356145.6, filed Nov. 26, 2008, U.S. Patent Application Ser. No. 61/201,648, filed Dec. 12, 2008, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "082016US01SequenceListingST25.txt", created on May 25, 2010, and having a size of 27,000 bytes and is filed concurrently with the specification. The sequence listing contained in this ASCII formatted document is part of the specification and is herein incorporated by reference in its entirety.

FIELD OF THE INVENTION

The present invention relates to materials and methods for the expression of a gene of interest specifically in seeds of plants, even more specifically in oilseed plants. In particular, the invention provides an expression cassette for regulating seed-specific expression in plants.

INTRODUCTION TO THE INVENTION

Plants use photosynthetically fixed carbon to support growth and to build up reserve products, such as starch or lipids. Storage oil (triacylglycerol) is a major plant product with great economical importance in human nutrition and as a renewable feedstock for various industrial products and bio-fuels. The world-wide production of vegetable oil is approximately 100 million metric tons in total per year, which mainly consists of soybean, oil palm, rapeseed and sunflower oil. Rapeseed production is increasing world-wide. The crop is mainly used for feed and food, but, increasingly, is being used in bio-diesel production. As a result of the great economic importance of vegetable oils and their expanded use as a renewable feedstock, there is considerable interest in the metabolic engineering of increased and/or modified seed oil content. In seeds of developing oil-seed rape (*Brassica napus* L.), sucrose is unloaded from the phloem and metabolized to glycolytic intermediates, such as hexose-phosphates, phosphoenolpyruvate and pyruvate, which are subsequently imported into the plastid and used for fatty acid synthesis. Free fatty acids are activated to coenzyme A (CoA) esters, exported from the plastid and used for the stepwise acylation of the glycerol backbone to synthesize triacylglycerol in the endoplasmic reticulum. In the first two steps of triacylglycerol (TAG) assembly, glycerol-3-phosphate (Gly3P) is acylated by Gly3P acyltransferase (GPAT) to lysophosphatidic acid, which is then acylated further by lysophosphatidic acid acyltransferase (LPAT) to phosphatidic acid. This is followed by dephosphorylation of phosphatidic acid by phosphatidic acid phosphohydrolase to release diacylglycerol (DAG), and the final acylation of diacylglycerol by DAG acyltransferase (DAGAT). Final storage of triacylglycerol occurs in endoplasmic reticulum-derived oil bodies.

Modification of oil-producing plants to alter and/or improve phenotypic characteristics (such as productivity or quality) requires the overexpression or down-regulation of endogenous genes or the expression of heterologous genes in plant tissues. Such genetic modification relies on the availability of a means to drive and to control gene expression as required. Indeed, genetic modification relies on the availability and use of suitable promoters which are effective in plants and which regulate gene expression so as to give the desired effect(s) in the transgenic plant. For numerous applications in plant biotechnology a tissue-specific expression profile is advantageous, since beneficial effects of expression in one tissue may have disadvantages in others. Seed-preferential or seed-specific promoters are useful for expressing or down-regulating genes as well as for producing large quantities of protein, and for producing oils or proteins of interest. It is advantageous to have the choice of a variety of different promoters so that the most suitable promoter may be selected for a particular gene, construct, cell, tissue, plant or environment. Moreover, the increasing interest in co-transforming plants with multiple transcription cassettes and the potential problems associated with using common regulatory sequences for these purposes require a variety of promoter sequences. There is, therefore, a great need in the art for the identification of novel sequences that can be used for expression of selected transgenes in economically important plants such as oil-producing plants. It is thus an objective of the present invention to provide new and alternative expression cassettes for seed-specific expression of transgenes in plants. This objective is solved by the present invention as herein further explained.

Cytochrome P450 mono-oxygenases, which catalyze substrate-, regio- and stereo-specific oxygenation steps in plant metabolism, have evolved to a huge superfamily of enzymes. Plant genome sequencing initiatives recently revealed more than 280 full length genes in *Arabidopsis thaliana*, 356 in rice and 312 in *Populus trichocarpa*. However, less than 20% of the coding sequences of the cytochrome P450 mono-oxygenases in the *A. thaliana* genome have been associated with a specific biochemical function.

SUMMARY OF THE INVENTION

During our investigation we were interested in the function of "orphan" cytochrome P450 enzymes. One particular enzyme family we characterized was the cytochrome P450 mono-oxygenase, CYP704 family, which consists of the two members CYP704A1 and CYP704A2. Remarkably an expression cassette comprising a chimeric CYP704A1 promoter—nucleic acid fusion and an expression cassette comprising a chimeric CYP704A2 promoter—nucleic acid fusion proved to be expressed specifically during the late stages of seed development. The invention described herein in the different embodiments, examples, figures and claims provides seed-specific promoters and promoter regions comprised in expression cassettes which can be used to direct heterologous gene expression in seeds. In one embodiment the invention provides an expression cassette for regulating seed-specific expression in plants comprising a promoter linked to a nucleic acid which is heterologous in relation to said promoter and wherein said promoter is selected from the group consisting of (a) SEQ ID NO: 1, SEQ ID NO: 2, SEQ ID NO: 13 or SEQ ID NO: 14 or a variant thereof, (b) a fragment of at least 50 consecutive bases of SEQ ID NO: 1, SEQ ID NO: 2, SEQ ID NO: 13 or SEQ ID NO: 14 having promoter activity, (c) a nucleotide sequence with at least 40% identity with SEQ ID NO: 1, SEQ ID NO: 2, SEQ ID NO: 13 or SEQ ID NO: 14 or the complement thereof and (d) a nucleotide sequence hybridizing under conditions equivalent to hybridization in 7% sodium dodecyl sulfate, 0.5 M NaPO$_4$, 1 mM EDTA at 50° C. with washing in 2×SSC, 0.1% SDS at 50° C. to a nucleotide sequence depicted in SEQ ID NO: 1, SEQ ID NO: 2, SEQ ID NO: 13 or SEQ ID NO: 14 or a fragment of at least 50 consecutive bases of SEQ ID NO: 1, SEQ ID NO: 2, SEQ ID NO: 13 or SEQ ID NO: 14 or the complement thereof. SEQ ID NO: 1 depicts the nucleotide sequence of the promoter of the cytochrome P450 704A1 gene from *A. thaliana*. SEQ ID NO: 2 depicts the nucleotide sequence of the promoter of the cytochrome P450 704A2 gene from *A. thaliana*. SEQ ID NO: 13 depicts the *Brassica napus* promoter (CYP704Bn promoter-3) of a *B. napus* cytochrome P450 704A2 homologous gene. SEQ ID NO: 14 depicts the *Brassica napus* promoter (CYP704Bn promoter-5) of a *B. napus* cytochrome P450 704A2 homologous gene.

The expression cassette can direct the expression of a protein, a polypeptide, a peptide, an antisense RNA, a sense RNA or a double-stranded RNA.

In another embodiment the invention provides a recombinant vector comprising an expression cassette as herein described before.

In a further embodiment the invention provides a transformed plant comprising an expression cassette of the invention or a recombinant vector of the invention.

The invention further provides transformed plants with the expression cassette or the recombinant vector of the invention. In a particular embodiment the transformed plant is a plant used for oil production. Particular plants are canola, maize, mustard, castor bean, sesame, cotton, linseed, soybean, *Arabidopsis*, *Phaseolus*, peanut, alfalfa, wheat, rice, oat, sorghum, rapeseed, rye, sugarcane, safflower, oil palms, flax, sunflower, *Brassica campestris*, *Brassica napus*, *Brassica juncea*, *Crambe abyssinica*.

Also provided are plant cells comprising an expression cassette of the invention and plant cells comprising a recombinant vector of the invention. In a particular embodiment microspores are provided comprising an expression cassette of the invention and microspores comprising a recombinant vector of the invention.

The invention also provides for a seed generated from the transformed plants wherein the seed comprises an expression cassette of the invention or a vector according to the invention.

Also provided is a method of producing a transformed plant with an expression cassette or a recombinant vector according to the invention, the method comprising providing an expression cassette or a vector of the invention transforming a plant with said expression cassette.

The invention further provides a method for producing a seed enhanced in product of a nucleic acid comprising (a) growing a transformed plant containing the expression vector of the invention, wherein said transformed plant produces said seed and said nucleic acid is transcribed in said seed, and (b) isolating said seed from said transformed plant. In a particular embodiment said nucleic acid encodes for a protein, a polypeptide, a peptide, the expression of an antisense RNA, a sense RNA or a double-stranded RNA.

In yet another embodiment the invention provides the use of SEQ ID NO: 3 or a variant or a functional fragment or a functional homologue with a least 85%, at least 90%, at least 95% identity with SEQ ID NO: 3 for the production of hydroxylated alkanes and hydroxylated fatty alcohols in a host cell. In other words the invention provides a process (or method) for the production of hydroxylated alkanes and hydroxylated fatty alcohols in a host cell comprising a) transforming said host cell with a chimeric construct comprising SEQ ID NO: 3 or a variant or a functional fragment or a functional homologue with at least 85%, at least 90%, at least 95% identity with SEQ ID NO: 3 operably linked to at least one suitable regulatory sequence, b) growing the transformed host cells of step a) and c) determining the presence or the absence of hydroxylated alkanes and hydroxylated fatty alcohols in the transformed cells of step b).

In a particular embodiment said host cell is a plant or plant cell.

In yet another particular embodiment said host cell is a yeast cell such as *Yarrowia lipolytica*, *Pichia pastoris*, *Saccharomyces cerevisiae*, a *Candida species*, a *Kluyveromyces species* or a *Hansenula species*.

In yet another embodiment the invention provides a chimeric construct comprising SEQ ID NO: 3 or a variant or a functional fragment or a functional homologue with a least 85%, at least 90%, at least 95% identity with SEQ ID NO: 3, operably linked to at least one suitable regulatory sequence. In yet another embodiment the invention provides an isolated host cell comprising a chimeric construct of the present invention.

DETAILED DESCRIPTION OF THE PREFERRED EMBODIMENTS

Figure 1:
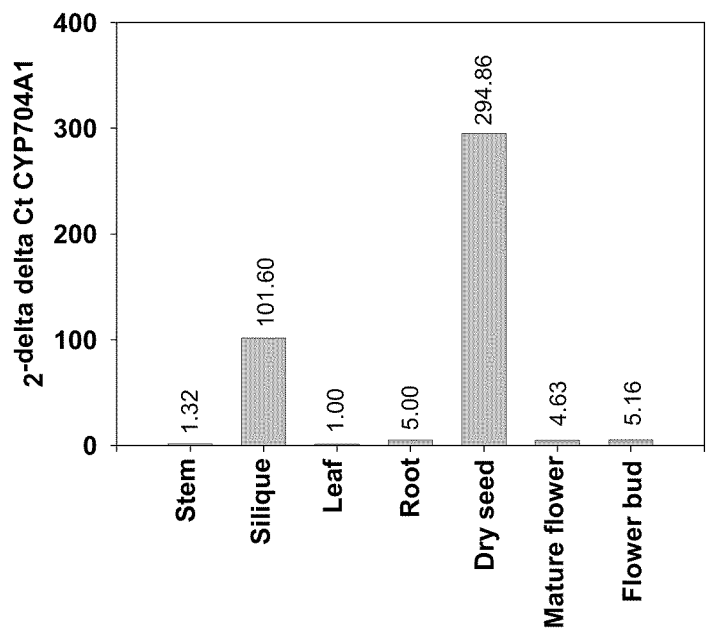
FIG. 1: Quantitative RT-PCR analysis of the expression of the CYP704A1 gene in different organs of *Arabidopsis thaliana*. The amounts of CYP704A1 transcripts ($2^{-\Delta\Delta Ct}$) are normalized to the endogenous reference ACTIN2. Data represent the mean of 3 samples with standard deviation. The experiment was repeated twice with similar results. Vertical bar chart representation of quantitative RT-PCR evaluation of the expression of CYP704A1 transcripts in different organs of *Arabidopsis thaliana*. The (data $2^{-\Delta\Delta Ct}$) were deduced by the Ct method.

The present invention provides expression cassettes capable of transcribing a heterologous nucleic acid sequence in a seed, and methods of modifying, producing, and using the same in plants. The present invention also provides compositions, transformed host cells, such as plants, containing an expression cassette with seed-specific promoters. The nucleotide sequence depicted in SEQ ID NO: 1 represents the nucleotide sequence of the promoter of the cytochrome P450 mono-oxygenase 704A1 gene (herein further designated as CYP704A1) of *Arabidopsis thaliana*. This gene is located on chromosome II and is described by the GenBank *A. thaliana* locus At2g44890. The nucleotide sequence depicted in SEQ ID NO: 2 represents the nucleotide sequence of the promoter of the cytochrome P450 mono-oxygenase 704A2 gene (herein further designated as CYP704A2) of *Arabidopsis thaliana*. This gene is located on chromosome II and is described by the GenBank *A. thaliana* locus At2g45510. Thus the invention provides an expression cassette for regulating seed-specific expression in plants comprising at least one transcription regulating nucleotide sequence derived from the *Arabidopsis thaliana* gene described by the GenBank genome locus At5g44890 or Atg45510 or its orthologous genes and operably (or "functionally") linked thereto at least one nucleic acid sequence which is heterologous in relation to said transcription regulating nucleotide sequence.

In one embodiment the invention provides a seed-specific promoter having the nucleotide sequence of SEQ ID NO: 1 from nucleotide position 1 to nucleotide position 1210 for use in an expression cassette. In a particular embodiment said seed-specific promoter has the nucleotide sequence of SEQ ID NO: 1 from nucleotide position 600 to nucleotide position 1210. In yet another particular embodiment said seed-specific promoter has the nucleotide sequence of SEQ ID NO: 1 from nucleotide position 800 to nucleotide position 1210. SEQ ID NO: 1 depicts the region upstream (i.e. located 5' upstream of) from the codon coding for the first amino acid of the CYP704A1 protein. Such a promoter region may be at least about 300 to about 400 to about 500 bp, at least about 1000 bp, at least about 1100 bp, at least about 1200 bp upstream of the start codon of the CYP704A1 gene. In another embodiment the invention provides a seed-specific promoter having the nucleotide sequence of SEQ ID NO: 2 from nucleotide position 1 to nucleotide position 920 for use in an expression cassette. In a particular embodiment said seed-specific promoter has the nucleotide sequence of SEQ ID NO: 2 from nucleotide position 450 to nucleotide position 920. In yet another particular embodiment said seed-specific promoter has the nucleotide sequence of SEQ ID NO: 2 from nucleotide position 700 to nucleotide position 920. SEQ ID NO: 2 depicts the region upstream (i.e. located 5' upstream of) from the codon coding for the first amino acid of the CYP704A2 protein. Such a promoter region may be at least about 300 to about 400 to about 500 bp, at least about 600 bp, at least about 700 bp, at least about 800 bp, at least about 900 bp upstream of the start codon of the CYP704A2 gene. In yet another embodiment the invention provides a *Brassica napus* seed-specific promoter having the nucleotide sequence of SEQ ID NO: 13 from nucleotide position 1 to nucleotide position 1953 for use in an expression cassette. In a particular embodiment said seed-specific promoter has the nucleotide sequence of SEQ ID NO: 13 from nucleotide position 1000 to nucleotide position 1953. In yet another particular embodiment said seed-specific promoter has the nucleotide sequence of SEQ ID NO: 13 from nucleotide position 1500 to nucleotide position 1953. SEQ ID NO: 13 depicts the region upstream (i.e. located 5' upstream of) from the codon coding for the first amino acid of the homologous *B. napus* CYP704A2 protein (Open Reading Frame 3, see Example 4). In yet another embodiment the invention provides a *Brassica napus* seed-specific promoter having the nucleotide sequence of SEQ ID NO: 14 from nucleotide position 1 to nucleotide position 3135 for use in an expression cassette. In a particular embodiment said seed-specific promoter has the nucleotide sequence of SEQ ID NO: 14 from nucleotide position 1000 to nucleotide position 3135. In yet another particular embodiment said seed-specific promoter has the nucleotide sequence of SEQ ID NO: 14 from nucleotide position 2000 to nucleotide position 3135. SEQ ID NO: 14 depicts the region upstream (i.e. located 5' upstream of) from the codon coding for the first amino acid of the homologous *B. napus* CYP704A2 protein (Open Reading Frame 5, see Example 4). Such a promoter region may be at least about 300 to about 400 to about 500 bp, at least about 600 bp, at least about 700 bp, at least about 800 bp, at least about 900 bp upstream of the start codon of the CYP704A2 gene or the *B. napus* homologous CYP704A2 genes.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding RNA. In a particular embodiment said RNA is mRNA and translation of this mRNA produces the corresponding gene product (i.e., a peptide, polypeptide, or protein). In another particular embodiment the heterologous nucleic acid, operably linked to the promoters of the invention, may also code for antisense RNA, sense RNA, double stranded RNA or synthetic microRNA molecules, according to rules well known in the art, to downregulate the expression of other genes comprised within the seed or even of genes present within a pathogen or pest that feeds upon the seeds of the transgenic plant.

The term "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e. does not naturally occur in that particular cell or organism).

The term "chimeric gene" refers to any gene that contains: a) DNA sequences, including regulatory and coding sequences that are not found together in nature, or b) sequences encoding parts of proteins not naturally adjoined, or c) parts of promoters that are not naturally adjoined. Accordingly, a chimeric gene may comprise regulatory sequences and coding sequences that are derived from different sources, or comprise regulatory sequences, and coding sequences derived from the same source, but arranged in a manner different from that found in nature. In the current invention a "homologous" gene or polynucleotide or polypeptide refers to a gene or polynucleotide or polypeptide that shares sequence similarity with the gene or polynucleotide or polypeptide of interest.

"Seed-specific" expression (or "transcription" which is equivalent) in the context of this invention means the transcription of a nucleic acid sequence by a promoter (or a transcription regulating element) in a way that transcription of said nucleic acid sequence in seeds contributes to more than 90%, preferably more than 95%, more preferably more than 99% of the entire quantity of the RNA transcribed from said nucleic acid sequence in the entire plant during any of its developmental stage.

"Seed-preferential" expression (or "transcription" which is equivalent) in the context of this invention means the transcription of a nucleic acid sequence by a transcription regulating element in a way that transcription of said nucleic acid sequence in seeds contributes to more than 50%, preferably more than 60%, more preferably more than 70%, even more preferably more than 80% of the entire quantity of the RNA transcribed from said nucleic add sequence in the entire plant during any of its developmental stages. The term "seed-enhanced" is equivalent to the term "seed-preferential".

The transcription sequences identified herein are found to mediate a strong expression specifically in seed. An expression cassette comprising SEQ ID NO: 1 and fragments thereof direct the expression specifically in siliques during seed development and in mature dry seeds. An expression cassette comprising SEQ ID NO: 2 and fragments thereof direct the expression specifically at the end of the seed development. More specifically, an expression cassette comprising SEQ ID NO: 2 and fragments thereof direct the expression specifically to begin between 7-11 days after fertilisation (DAF), with a maximum of expression at the end of maturation (>15 DAF), decrease in dry seed and increase again after 2 hours imbibition in mature seed and decreasing again upon germination. A seed is representing an embryo in its shell, or the embryo is a part of the seed. In the context of this invention, the term seed-specific therefore also means embryo-specific. The terms seed-specific and embryo-specific can be used interchangeable herein.

"Seed" means a seed of a plant in any stage of its development i.e. starting from the fusion of pollen and oocyte, continuing over the embryo stage and the stage of the dormant seed, until the germinating seed, ending with early seedling organs, as e.g. cotyledons and hypocotyls. "Microspore"—in seed plants—corresponds to the developing pollen grain at the uninucleate stage.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

As used herein, "promoter" means a region of DNA sequence that is essential for the initiation of transcription of DNA, resulting in the generation of an RNA molecule that is complimentary to the transcribed DNA; this region may also be referred to as a "5' regulatory region." Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see US5641876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

Confirmation of promoter activity for a functional promoter fragment in seed may be determined by those skilled in the art, for example using a promoter-reporter construct comprising the genomic sequence operably linked to a beta-glucuronidase (GUS) reporter gene as herein further explained. The seed-preferential expression capacity of the identified or generated fragments of the promoters of the invention can be conveniently tested by operably linking such DNA molecules to a nucleotide sequence encoding an easy scorable marker, e.g. a beta-glucuronidase gene, introducing such a chimeric gene into a plant and analyzing the expression pattern of the marker in seeds as compared with the expression pattern of the marker in other parts of the plant. Other candidates for a marker (or a reporter gene) are chloramphenicol acetyl transferase (CAT) and proteins with fluorescent properties, such as green fluorescent protein (GFP) from *Aequora victoria*. To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the seed-specific functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

Instead of measuring the activity of a reporter enzyme, the transcriptional promoter activity (and functionality) can also be determined by measuring the level of RNA that is produced. This level of RNA, such as mRNA, can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with 2, 3, 4, or more tissues or organs selected from the group consisting of floral tissue, floral apex, pollen, leaf, embryo, shoot, leaf primordia, shoot apex, root, root tip, vascular tissue and cotyledon. As used herein, examples of plant organs are seed, leaf, root, etc. and example of tissues are leaf primordia, shoot apex, vascular tissue, etc. The activity or strength of a promoter may be measured in terms of the amount of mRNA or protein accumulation it specifically produces, relative to the total amount of mRNA or protein. The promoter preferably expresses an operably linked nucleic acid sequence at a level greater than about 1%, about 2%, more preferably greater than about 5, 6, 7, 8, or about 9%, even more preferably greater than about 10, 11, 12, 13, 14, 15, 16, 17, 18, or about 19%, and most preferably greater than about 20% of the total mRNA. Alternatively, the activity or strength of a promoter may be expressed relative to a well-characterized promoter (for which transcriptional activity was previously assessed).

It will herein further be clear that equivalent CYP704A1 and CYP704A2 promoters can be isolated from other plants. To this end, orthologous promoter fragments may be isolated from other plants using SEQ ID NO: 1 or SEQ ID NO: 2 or a functional fragment having at least 50 consecutive nucleotides thereof as a probe and identifying nucleotide sequences from these other plants which hybridize under the herein described hybridization conditions. By way of example, a promoter of the invention may be used to screen a genomic library of a crop or plant of interest to isolate corresponding promoter sequences according to techniques well known in the art. Thus, a promoter sequence of the invention may be used as a probe for hybridization with a genomic library under medium to high stringency conditions. As an alternative equivalent promoters can be isolated using the coding sequences of CYP704A1 and/or CYP704A2 to screen a genomic library (e.g. by hybridization or in silico) of a crop of interest. When sufficient identity between the coding sequences is obtained (as a rule higher than 85% identity) then promoter regions can be isolated upstream of the orthologous CYP704A1 and/or orthologous CYP704A2 genes. The present invention provides an example to clone orthologous promoters from Brassica napus in example 4.

The term "hybridization" refers to the ability of a first strand of nucleic acid to join with a second strand via hydrogen bond base pairing when the two nucleic acid strands have sufficient sequence identity. Hybridization occurs when the two nucleic acid molecules anneal to one another under appropriate conditions. Nucleic acid hybridization is a technique well known to those of skill in the art of DNA manipulation. The hybridization property of a given pair of nucleic acids is an indication of their similarity or identity. Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence. "Stringent hybridization conditions" and "stringent hybridization wash conditions" in the context of nucleic acid hybridization experiments such as Southern and Northern hybridization are sequence dependent, and are different under different environmental parameters. An example of highly stringent wash conditions is 0.15 M NaCl at 72° C. for about 15 minutes. An example of stringent wash conditions is a 0.2×SSC wash at 65° C. for 15 minutes, Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na on concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic adds that do not hybridize to each other under stringent conditions are still substantially identical if the proteins that they encode are substantially identical. This occurs, e.g., when a copy of a nucleic add is created using the maximum codon degeneracy permitted by the genetic code. Very stringent conditions are selected to be equal to the $T_m$ for a particular probe. An example of stringent conditions for hybridization of complementary nucleic adds which have more than 100 complementary residues on a filter in a Southern or Northern blot is 50% formamide, e.g., hybridization in 50% formamide, 1 M NaCl 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide, sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS). 0.5 M NaPO$_4$, 1 mM EDTA at 50° C. with washing in 0.5×SSC, 0.1% SDS at 50° C., even more desirably still in 7% sodium dodecyl sulfate (SDS), 0.5 M NaPO$_4$, 1 mM EDTA at 50° C. with washing in 0.1×SSC, 0.1% SDS at 50° C.

In another embodiment of the present invention seed-specific promoters are provided which comprise a nucleotide sequence having at least 40%, at least 50%, or at least 60%, or at least 70%, or at least 80%, or at least 90%, or at least 95% sequence identity to the herein described promoters and promoter regions. The term "variant" with respect to the transcription regulating nucleotide sequences SEQ ID NO: 1, 2, 13 and 14 of the invention is intended to mean substantially similar sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of SEQ ID NO: 1, 2, 13 or 14. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, 3$^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules. As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

The promoters of the present invention may be operably linked to a nucleic acid sequence that is heterologous with respect to the promoter. The nucleic acid sequence may generally be any nucleic acid sequence for which an increased level or altered level (e.g. in a different organ) of transcription is desired. The nucleic acid sequence can for example encode a polypeptide that is suitable for incorporation into the diet of a human or an animal or can provide some other agricultural or industrial important feature. Suitable heterologous nucleic acid sequences include, without limitation, those encoding seed storage proteins, fatty acid pathway enzymes, epoxidases, hydroxylases, cytochrome P450 mono-oxygenases, desaturases, tocopherol biosynthetic enzymes, carotenoid biosynthesis enzymes, amino acid biosynthetic enzymes, steroid pathway enzymes, and starch branching enzymes.

In another embodiment the invention provides a vector, in particular a recombinant vector comprising an expression cassette of the invention. A "recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

Thus, any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. No. 4,971,908, U.S. Pat. No. 4,940,835, U.S. Pat. No. 4,769,061 and U.S. Pat. No. 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. Plant functional promoters useful for specific expression in seed include those from plant storage proteins and from proteins involved in fatty acid biosynthesis in oilseeds. Examples of such promoters include the 5' regulatory regions from such structural nucleic acid sequences as napin, phaseolin, zein, soybean trypsin inhibitor, ACP, stearoyl-ACP desaturase, and oleosin. Seed-specific regulation is further discussed in EP0255378. Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco. An additional promoter is preferably seed selective, tissue selective, constitutive, or inducible.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

The present invention is also directed to transgenic plants and transformed host cells which comprise a promoter operably linked to a heterologous nucleic acid sequence. Other nucleic acid sequences may also be introduced into the plant or host cell along with the promoter and structural nucleic acid sequence. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

The term "transformation" herein refers to the introduction (or transfer) of nucleic acid into a recipient host such as a plant or any plant parts or tissues including plant cells, protoplasts, calli, roots, tubers, seeds, stems, leaves, seedlings, embryos, pollen and microspores. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having an introduced nucleic acid stably introduced into a genome of the plant, for example, the nuclear or plastid genomes.

In some embodiments of the present invention, one or more components of a plant, cell, or organism are compared to a plant, cell, or organism having a "similar genetic background." In a preferred aspect, a "similar genetic background" is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

A transformed host cell may generally be any cell that is compatible with the present invention. A transformed host plant or cell can be or derived from a monocotyledonous plant or a dicotyledonous plant including, but not limited to canola, maize, mustard, castor bean, sesame, cotton, linseed, soybean, *Arabidopsis*, *Phaseolus*, peanut, alfalfa, wheat, rice, oat, sorghum, rapeseed, rye, sugarcane, safflower, oil palms, flax, sunflower, *Brassica campestris*, *Brassica napus*, *Brassica juncea*, *Crambe abyssinica*. In a particularly preferred embodiment, the plant or cell is or derived from canola. In another particularly preferred embodiment, the plant or cell is or derived from *Brassica napus*.

A second part of the invention deals with the properties of CYP704A2 for the modification of fatty acids, alkanols and alkanes. The most abundant fatty acids in agronomically important plant seeds are fatty acids with a chain length of C16 and C18 possessing between 0 and 3 double bonds in cis configuration. One industrially important modification is the oxygenation of the fatty acid, in particular the end hydroxylation (omega-hydroxylation) of the fatty acid is often desired. The extra addition of an oxygen atom renders the fatty acid more polar but most importantly the extra oxygen atom creates the possibility of forming a covalent linkage with a carboxylic group or with another hydroxyl group of a neighboring fatty acid. In addition to the potential engineering of the biosynthesis of plant biopolymers and waxes, alkane oxidation is desired because it offers the possibility of many applications based on fossil resources and can be a useful tool for bioremediation purposes. During the characterization of the enzymatic function of cytochrome CYP704A2 of *Arabidopsis thaliana* we have identified that this enzyme can convert alkanes into alkane alcohols (i.e. alkanols), alkane diols and hydroxyl fatty acids (i.e. fatty acids comprising at least one hydroxyl group).

In yet another embodiment the invention provides the use of SEQ ID NO: 3 or a variant or a functional fragment or a functional homologue with a least 85%, at least 90%, at least 95% identity with SEQ ID NO: 3 for the production of alkanols, alkane diols and hydroxyl fatty acids in a host cell. In other words the invention provides a process (or method) for the production of alkanols, alkane diols and/or hydroxyl fatty acids in a host cell comprising a) transforming said host cell with a chimeric construct comprising SEQ ID NO: 3 or a variant or a functional fragment or a functional homologue with at least 85%, at least 90%, at least 95% identity with SEQ ID NO: 3 operably linked to at least one suitable regulatory sequence, b) growing the transformed host cells of step a) and c) determining the presence or the absence of alkanols, alkane diols and/or hydroxyl fatty acids in the transformed cells of step b).

In a particular embodiment said host cell is a plant or plant cell.

In yet another particular embodiment said host cell is a yeast cell such as *Yarrowia lipolytica*, *Pichia pastoris*, *Saccharomyces cerevisiae*, a *Candida species*, a *Kluyveromyces species*, a *Hansenula species*, and the like.

In yet another embodiment the invention provides a method for the production of alkanols, alkan-diols and hydroxyl fatty acids said method comprising contacting alkanes with CYP704A2. In a particular embodiment said production of alkanols, alkan-diols and hydroxyl fatty acids occurs in vivo in plant seeds that comprise alkanes. In another particular embodiment said production of alkanols, alkan-diols and hydroxyl fatty acids occurs in vitro through incubation with a source of the CYP704A2 enzyme which can be a purified source or a recombinant source. The amino acid sequence of the CYP704A2 enzyme is depicted in SEQ ID NO: 4.

In yet another embodiment the invention provides a chimeric construct comprising SEQ ID NO: 3 or a variant or a functional fragment or a functional homologue with at least 85%, at least 90%, at least 95% identity with SEQ ID NO: 3, operably linked to at least one suitable regulatory sequence. In yet another embodiment the invention provides an isolated host cell comprising a chimeric gene of the present invention.

Throughout the description and examples, reference is made to the following sequences represented in the sequence listing:

SEQ ID NO: 1: nucleotide sequence of the promoter of the CYP704A1 gene of *Arabidopsis thaliana*

SEQ ID NO: 2: nucleotide sequence of the promoter of the CYP704A2 gene of *Arabidopsis thaliana*

SEQ ID NO: 3: mRNA sequence of the CYP704A2 gene of *Arabidopsis thaliana*

SEQ ID NO: 4: amino acid sequence of the CYP704A2 gene of *Arabidopsis thaliana*

SEQ ID NO: 5: forward primer for amplification of SEQ ID NO: 1

SEQ ID NO: 6: reverse primer for amplification of SEQ ID NO: 1

SEQ ID NO: 7: first forward primer for amplification of SEQ ID NO: 3

SEQ ID NO: 8: first reverse primer for amplification of SEQ ID NO: 3

SEQ ID NO: 9: second forward primer for amplification of SEQ ID NO: 3

SEQ ID NO: 10: second reverse primer for amplification of SEQ ID NO: 3

SEQ ID NO: 11: forward primer for amplification of SEQ ID NO: 2

SEQ ID NO: 12: reverse primer for amplification of SEQ ID NO: 2

SEQ ID NO: 13: *Brassica napus* promoter-3 (CYP704Bn-3)

SEQ ID NO: 14: *Brassica napus* promoter-5 (CYP704Bn-5)

EXAMPLES

Materials and General Methods

Unless indicated otherwise, chemicals and reagents in the examples were obtained from Sigma Chemical Company, restriction endonucleases were from Fermentas or Roche-Boehringer, and other modifying enzymes or kits regarding biochemicals and molecular biological assays were from Qiagen, Invitrogen and Q-BIOgene. Bacterial strains were from Invitrogen. The cloning steps carried out for the purposes of the present invention, such as, for example, restriction cleavages, agarose gel electrophoresis, purification of DNA fragments, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger. Any number of methods well known to those skilled in the art can be used to isolate fragments of a DNA molecule disclosed herein. For example, PCR (polymerase chain reaction) technology can be used to amplify flanking regions from a genomic library of a plant using publicly available sequence information. A number of methods are known to those of skill in the art to amplify unknown DNA sequences adjacent to a core region of known sequence. Methods include but are not limited to inverse PCR, vectorette PCR, Y-shaped PCR, and genome walking approaches. DNA molecule fragments can also be obtained by other techniques such as by directly synthesizing the fragment by chemical means, as is commonly practiced by using an automated oligonucleotide synthesizer. For the present invention, the DNA molecules were isolated by designing PCR primers based on available sequence information. Standard materials and methods for plant molecular work are described in Plant Molecular Biology Labfax (1993) by R. D. D. Croy, jointly published by BIOS Scientific Publications Ltd (UK) and Blackwell Scientific Publications.

Chemicals—The silylating reagent N,O-bistrimethylsilyl-trifluoroacetamide containing 1% of trimethylchlorosilane was from Pierce (Rockfold, Ill.). NADPH was from Sigma (Saint Louis, Mo.). Thin layer plates (Silica Gel G60 F254; 0.25 mm) were from Merck (Darmstadt, Germany).

Heterologous expression of CYP704A2 in Yeast—For functional expression of the full length CYP704A2 clone, we used a yeast expression system specifically developed for the expression of P450 enzymes and consisting of plasmid pYeDP60 and *Saccharomyces cerevisiae* WAT11 strain (Pompon D. et al (1996) Methods Enzymol 272, 51-64). Yeast cultures were grown and CYP704A2 expression was induced as described in Pompon et al. (1996) see above from one isolated transformed colony. After growth, cells were harvested by centrifugation and manually broken with glass beads (0.45 mm diameter) in 50 mM Tris-HCl buffer (pH 7.5) containing 1 mM EDTA and 600 mM sorbitol. The homogenate was centrifuged for 10 min at 10,000 g. The resulting supernatant was centrifuged for 1 h at 100,000 g. The pellet consisting of microsomal membranes was resuspended in 50 mM Tris-HCl (pH 7.4), 1 mM EDTA and 30% (v/v) glycerol with a Potter-Elvehjem homogenizer and stored at −30° C. The volume of resuspension buffer is proportional to the weight of yeast pellet: microsomes extracted from 6 g of yeast are resuspended in 3 ml of buffer. All procedures for microsomal preparation were carried out at 0-4° C. The cytochrome P450 content was measured by the method of Omura and Sato (1964) J Biol Chem 239, 2370-2378.

Plant material and microsomal preparation—After sterilization, *Arabidopsis* (ecotype Col-0) seeds were grown on Murashige and Skoog medium (MS medium 4.2 g/l, sucrose 10 g/l, pastagar B 8 g/l, myoinositol 100 mg/l, thiamine 10 mg/l, nicotinic acid 1 mg/l and pyridoxine 1 mg/l—final pH 5.7) during five weeks. *Arabidopsis* plants (approximately 10 g) were homogenized with mortar and pestle in 50 ml of extraction buffer (250 mM tricine, 50 mM $NaHSO_3$, 5 g/l bovine serum albumin, 2 mM EDTA, 100 mM ascorbic acid and 2 mM dithiothreitol—final pH 8.2). The homogenate was filtered through 50 μm nylon filtration cloth and centrifuged for 10 min at 10,000 g. The resulting supernatant was centrifuged for 1 h at 100,000 g. The supernatant (cytosol) was directly stored at −30° C. and the microsomal pellet was resuspended in the buffer at pH 8.2 (50 mM NaCl, 100 mM tricine, 250 mM sucrose, 2 mM EDTA and 2 mM dithiothreitol), with a Potter-Elvehjem homogenizer and stored at −30° C. All procedures for microsomal preparation were carried out at 0-4° C.

Enzyme activities—radiolabeled substrates were dissolved in ethanol that was evaporated before the addition of microsomes into the glass tube. Resolubilization of the substrates was confirmed by measuring the radioactivity of the incubation media. Enzymatic activities of CYP704A2 from transformed yeast or *Arabidopsis* microsomes were determined by following the formation rate of metabolites. The standard assay (0.1 ml) contained 20 mM sodium phosphate (pH 7.4), 1 mM NADPH, and radiolabeled substrate (100 µM). The reaction was initiated by the addition of NADPH and was stopped by the addition of 20 µl acetonitrile (containing 0.2% acetic acid). The reaction products were resolved by TLC or HPLC as described below.

Thin layer chromatographic (TLC) methods—Incubation media were directly spotted on TLC plates. For separation of metabolites from residual substrate, TLC were developed with a mixture of diethyl ether/light petroleum (boiling point, 40-60° C.)/formic acid (50:50:1, v/v/v). The plates were scanned with a radioactivity detector (Raytest Rita Star). The area corresponding to the metabolites were scraped into counting vials and quantified by liquid scintillation, or they were eluted from the silica with 10 ml of diethyl ether, which was removed by evaporation. They were then subjected to GC/MS analysis.

GC/MS analysis—GC-MS analysis were carried out on a gas chromatograph (Agilent 6890 Series) equipped with a 30-m capillary column with an internal diameter of 0.25 mm and a film thickness of 0.25 µm (HP-5MS). The gas chromatograph was combined with a quadrupole mass selective detector (Agilent 5973N). Mass spectra were recorded at 70 eV and analysed as in Eglinton et al. (1968) Org. Mass. Spectrom 1, 593-611.

1. PCR Quantification of CYP704A1 and CYP704A2 Expression in *Arabidopsis thaliana*

Total RNA was extracted from stems, siliques, leave, roots, dry seeds, mature flowers, petals flower buds, immature seed and seed during germination of *A. thaliana* wild type Col-0 plants were purified using "Total RNA" kit from Macherey-Nagel products. Synthesis of cDNA by RT-PCR was carried out using the SuperScript™ III Reverse Transcriptase kit from Invitrogen™ following the Invitrogen protocol. Briefly, 13 µl of water containing 2 µg of total extracted mRNA, 500 µM of dNTP mix were heated at 65° C. for 5 min. Then, 200 ng of random primers, 50 µM of DTT, 40 U of RNase OUT™ recombinant RNase inhibitor, 200 U of Superscript™ III RT, 1× First Strand Buffer final concentration were added in a final volume of 20 µl. The mixture was then incubated during 30-60 min at 50° C. Q-PCR was performed using specific primers pairs allowing for specific hybridization to the cDNAs of CYP704A1 and CYP704A2. Nucleotide sequences of the primers are for CYP704A1: Forward 5'-GG-TATACTCCTGTACACGCCACAA-3' (SEQ ID NO: 5, 29% mismatch with the nucleotide sequence of CYP704A2) and Reverse 5'-CCTGAAAGTAGGCTTTGTCCTC-3' (SEQ ID NO: 6, 27% mismatch with the nucleotide sequence of CYP704A2). For CYP704A2, two sets of probes were selected. The first hybridizes a region with homology to CYP704A1: forward 5'-CAGTAGTAGAGAGAATATGGC-3' (SEQ ID NO: 7, 28% mismatch with the nucleotide sequence of CYP704A1) and reverse 5'-CTCTAGTA-GAGAACTCAAAGC-3' 3' (SEQ ID NO: 8, 7% mismatch with the nucleotide sequence of CYP704A1). The second set of probes, used as a control, is more selective since the forward primer hybridizes on the first 18 nucleotides of CYP704A2. Those first nucleotides have no nucleotide identity in the two genes. Forward primer of the set 2 is 5'-ATG-GAGATTTTGACGAGCATAGC-3' (SEQ ID NO: 9, 78% mismatch with the nucleotide sequence of CYP704A1) and reverse sequence 5'-CATAAGATAGATAGTGAAACA-CAAAACG-3' (SEQ ID NO: 10, 25% mismatch with the nucleotide sequence of CYP704A1). The software used to design the oligonucleotide sequences was Primer Express. The q-PCR program used for these experiments was 2 min at 50° C., 10 min at 95° C., and 40 cycles of 15 sec at 95° C. and 1 min at 60° C. Q-PCR reactions were carried out at least in triplicate with 1 µl of cDNA for each organ sample and with CyberGreen as fluorescent probe. ACTIN 2 of *Arabidopsis thaliana* (GenBank locus At5g09810) was used as an internal control for data normalization. The relative transcript levels for each gene were expressed as ratios to ACTIN2 normalized transcript levels in each organ.

Figure 2:
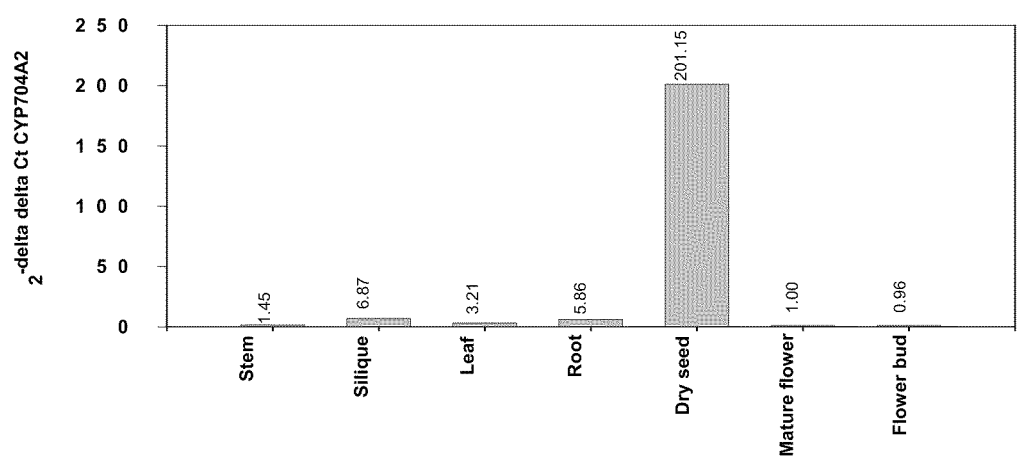
FIG. 2: Quantitative RT-PCR of the expression of CYP704A2 gene in different organs of *Arabidopsis thaliana*. The amounts of CYP704A2 transcripts ($2^{-\Delta\Delta Ct}$) are normalized to the endogenous reference ACTIN2. Data represent mean of 3 samples with standard deviation. The experiment was repeated twice with similar results. Vertical bar chart representation of qRT-PCR evaluation of the expression of CYP704A2 transcripts in different organs of *Arabidopsis thaliana*. The (data $2^{-\Delta\Delta Ct}$) were deduced by the Ct method.
Figure 3:
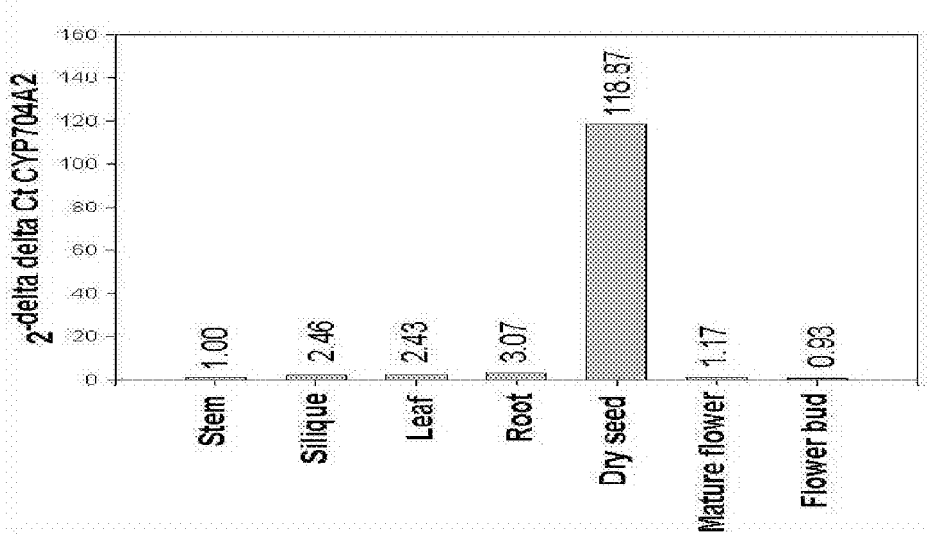
FIG. 3: Quantitative RT-PCR of the expression of CYP704A2 gene in different organs of *Arabidopsis thaliana* with a 5'-terminal specific probe. The amounts of CYP704A2 transcripts ($2^{-\Delta\Delta Ct}$) are normalized to the endogenous reference ACTIN2. Data represent mean of 3 samples with standard deviation. The experiment was repeated twice with similar results. Vertical bar chart representation of qRT-PCR evaluation of the expression of CYP704A2 transcripts in different organs of *Arabidopsis thaliana* with a 5'-terminal specific primer. The (data $2^{-\Delta\Delta Ct}$) were deduced by the Ct method.
Figure 4:
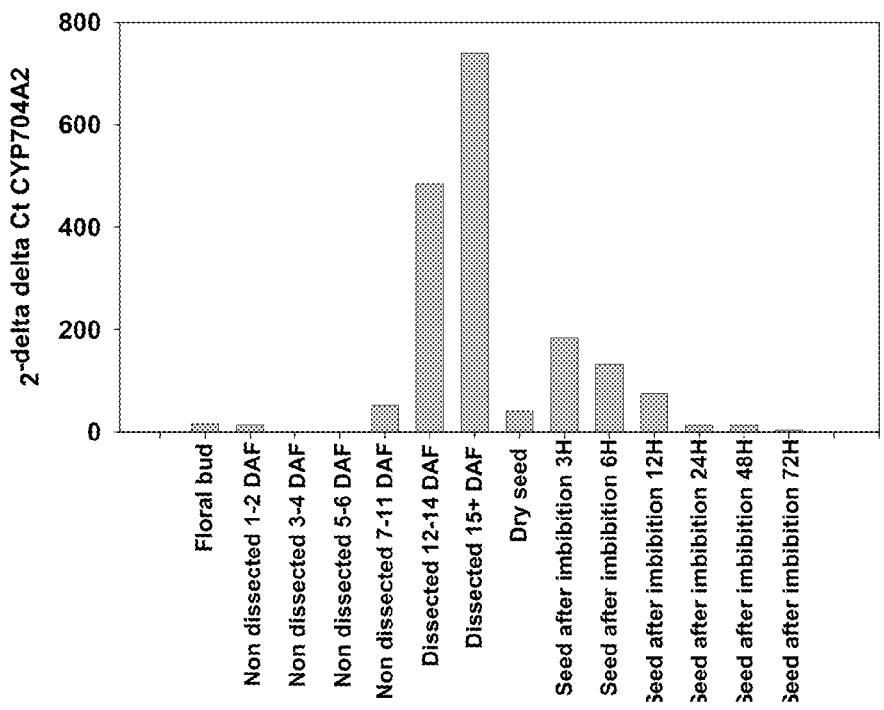
FIG. 4: Quantitative RT-PCR of the expression of CYP704A2 gene during seed development from floral bud to dry seed, and during seed germination of *Arabidopsis thaliana*. The amounts of CYP704A2 transcripts ($2^{-\Delta\Delta Ct}$) are normalized to the endogenous reference ACTIN2. Data represent mean of 3 samples with standard deviation. The experiment was repeated twice with similar results. Vertical bar chart representation of qRT-PCR evaluation of the evolution of the expression of CYP704A2 transcripts during seed development from floral bud to dry seed, and during seed germination after imbibition with the CYP704A2 primer. The (data $2^{-\Delta\Delta Ct}$) were deduced by the Ct method.
Figure 5:
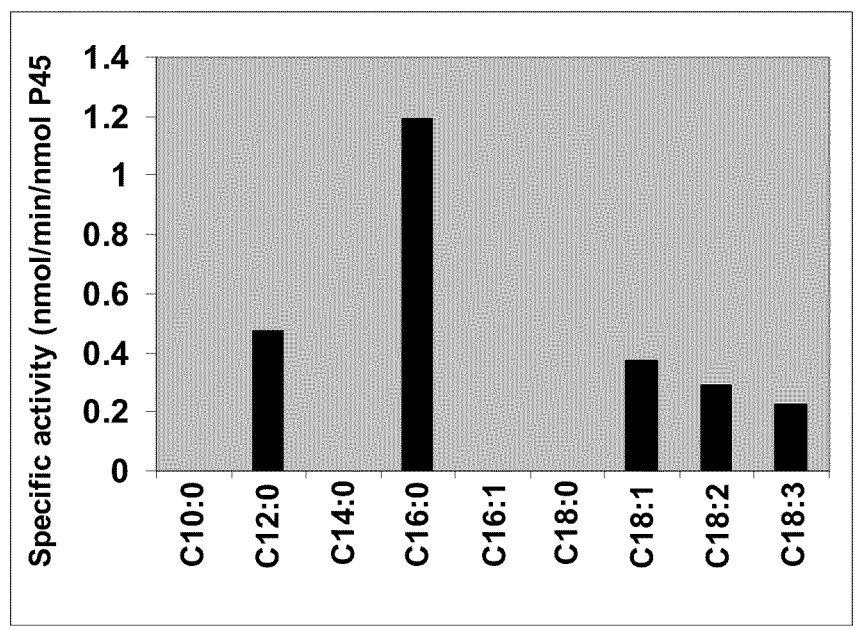
FIG. 5: Fatty acid hydroxylase activity of CYP704A2. Microsomes prepared from yeast expressing CYP704A2 were incubated with 100 µM of radiolabeled substrates. Incubations were carried out for 20 min at 27° C. and contained 78 pmoles of CYP704A2. Activities were determined as described in the examples by monitoring on TLC the formation of the metabolites.

Because of the strong identity of sequence between CYP704A1 and CYP704A2, q-PCR probes were designed so as to maximize the specificity of hybridization. The analysis of the melting curves obtained for the selected couples of primers indicated a strong specificity of hybridization, as indicated by a single melting point. A strong expression of both CYP704A1 and CYP704A2 was detected in seeds (respectively FIG. 1 and FIG. 2). Comparing the levels of the transcripts in the different organs, CYP704A1 appeared specifically expressed in the siliques during seed development and in the mature dry seeds. Expression in the other organs tested was very low. CYP704A2 is seed specific and highest CYP704A2 expression is rather at the end of the seed development. To confirm these data, the experiment was repeated with the second set of primers, more specific to CYP704A2. Similar results were obtained as can be seen in FIG. 3. It thus appears that the probe-sets are specific to the CYP704A1 and CYP704A2 genes. CYP704A2 shows the most restricted expression in mature seeds. A more detailed analysis of the RNA expression of CYP704A2 (FIG. 5) revealed an increase of the expression beginning from 7-11 DAF, with a maximum of expression at the end of maturation (15+). Transcripts decrease in dry seed and increase again after 2 hours of imbibition of mature seed. Transcripts decrease after longer imbibition and upon germination.

2. Generation of an Expression Cassette Comprising a Seed Specific Promoter of *Arabidopsis thaliana*

To isolate a promoter fragment of CYP704A2 (depicted in SEQ ID NO: 2), genomic DNA was isolated from *Arabidopsis thaliana* (ecotype Columbia), as described (Galbiati M et al (2000) Funct. Integr. Genomics 1(1):25-34). The isolated genomic DNA was employed as matrix DNA for a polymerase chain reaction (PCR) mediated amplification using the oligonucleotide primers and protocols indicated below. The primers used for amplification comprised respectively BamHI and HindIII restriction sites.

Amplification is carried out as follows:
10 ng genomic DNA of *Arabidopsis thaliana*
1×PCR buffer
1.5 mM MgCl$_2$,
200 µM each of dATP, dCTP, dGTP and dTTP
10 pmol of each oligonucleotide primers:

```
Forward:
                                      (SEQ ID No: 11)
5'-CGAAGCTTAAGCTTGCAATCTCTCAGATACTTG-3'

Reverse:
                                      (SEQ ID No: 12)
5'-GGGATCCACTTCGAAGTCAACGATAGTATC-3'
```

3.5 Units Isis DNA polymerase (Invitrogen) in a final volume of 50 μl

The following temperature program was employed for the various amplifications (BIORAD Thermocycler).
1. 96° C. for 10 min
2. 58° C. for 2 min, followed by 72° C. for 3 min and 96° C. for 3 min. Repeated 30 times.
3. 58° C. for 1 min, followed by 72° C. for 10 min.
4. Storage at 4° C.

Sequence verification of the PCR product resulted in the nucleotide sequence as depicted in SEQ ID NO: 2.

The resulting PCR-product was digested with BamHI and HindIII and inserted into the pBi101 vector (Clontech) which was also digested with the same restriction enzymes (which recognition sites are present in the multi-cloning site of the vector). The vector pBi101 contains a promoter-less GUS gene downstream of a multi-cloning site. In the resulting recombinant pBi101 vector the GUS gene was brought under transcriptional control of a CYP704A2 promoter fragment. Thus, the CYP704A2-promoter fragment (909 base pairs (bp) situated upstream of the startcodon of the CYP704A2 sequence, i.e. SEQ ID NO: 3)—GUS (a gene encoding beta-glucuronidase) construct is an expression cassette which was cloned in the plant transformation vector pBi101.

3. Expression Profile of the CYP704A2 Promoter:GUS Construct in Stably Transformed *Arabidopsis thaliana* Plants In a next step the recombinant vector comprising the expression cassette of example 2 was used to stably transform *Arabidopsis thaliana*. The protocol for *Agrobacterium* mediated transformation of *A. thaliana* was according to the floral dip method described by Clough S J and Bent A F (1998) Plant J 16(6): 735-43. β-glucuronidase activity was monitored in planta with the chromogenic substrate X-Glue (5-bromo-4-Chloro-3-indolyl-β-D-glucuronic acid) during corresponding activity assays (Jefferson R A et al (1987) EMBO J. 20; 6(13):3901-7). For determination of promoter activity and tissue specificity plant tissue is dissected, embedded, stained and analyzed as described (e.g., Bäumlein H et al (1991) Mol. Gen. Genetics 225(3):459-67). Thus, the activity of beta-glucuronidase in the transformed plants was witnessed by the presence of the blue color due to the enzymatic metabolism of the substrate X-Gluc.

GUS staining was carried out on dissected mature seed after 2 hours of imbibition of the seed. It was observed that the expression was essentially located in the cotyledons and also in the apical root meristem. The profile of expression confirms the q-PCR experiments of example 1.

4. Isolation of Orthologous Promoters from *Brassica napus*

Five open reading frames (ORF1, -2, -3, -4 and -5) were identified, in our proprietary *Brassica napus* gene sequence databank, which possess a high degree of identity with the *A. thaliana* CYP704A2 mRNA sequence depicted in SEQ ID NO: 3. Corresponding promoters, which direct the expression of ORF1, -2, -3, -4 and -5, were identified based on in silico genome walking in the genomic sequence of *B. napus*, followed by isolation of these five promoters with PCR cloning. Promoter sequences of approximately 2-3 kb (i.e. about 2000-3000 base pairs before the start codon) were obtained resulting in CYP704Bn-promoter 1, -2, -3, -4 and -5. Promoters CYP704Bn-3 (depicted in SEQ ID NO: 13) and CYP704Bn-5 (depicted in SEQ ID NO: 14) were withheld based on the specific activation of these promoters in seeds as witnessed by the embryo-specific occurrence of the ORF-3 and ORF-5. Indeed, from a BLAST search on the *B. napus* embryo transcriptome databases it was concluded that only ORF-3 and ORF-5 are expressed in the *B. napus* PPS02 (Bayer tester line) embryo. We therefore considered the corresponding promoter fragments for directing a seed-specific expression.

Four different chimeric genes were constructed wherein SEQ ID NO: 13 (CYP704Bn-3 promoter) and SEQ ID NO: 14 (CYP704Bn-5 promoter) are genetically fused to respectively the GUS (beta-glucuronidase) open reading frame, in the vector pTOF13, and respectively the EGFP (enhanced green fluorescent protein) open reading frame, in the vector pCO274.

In a next step *B. napus* is genetically transformed with plant transformation vectors comprising the above chimeric genes using methods known in the art. The seed-specific expression of the chimeric genes is observed in seeds of stably transformed *B. napus* plants.

5. Characterisation of the *B. napus* Seed-Specific Promoters

DoOP (on the internet at doop.abc.huon), databases of Orthologous Promoters, Barta E. et al (2005) *Nucleic Acids Research* Vol. 33, D86-D90) is a bioinformatics tool to identify the conserved sequence blocks (consensus sequences or consensus motifs) between orthologous eukaryotic promoter sequences. The two *A. thaliana* promoters (CYP704A1, CYP704A2) and the five *B. napus* promoters (CYP704Bn-1, -2, -3, -4 and -5) were analyzed for the presence of promoter consensus sequences (i.e. sequence motifs). The analysis shows that the *B. napus* promoters CYP704Bn-3 (SEQ ID NO: 13) and CYP704Bn-5 (SEQ ID NO: 14) share the highest number of sequence motifs with the *A. thaliana* promoter CYP704A2 (SEQ ID NO: 2). We conclude that the *B. napus* promoters CYP704Bn-3 and CYP704Bn-5 represent the orthologous promoters of the *A. thaliana* CYP70A2 promoter.

TABLE 1

| Motif ID | Motif length | Consensus | CYP704Bn-3 | CYP704Bn-5 | CYP704A1 | CYP704A2 | CYP704Bn-1 | CYP704Bn-2 | CYP704Bn-4 |
|---|---|---|---|---|---|---|---|---|---|
| m1 | 15 | CTCTCAGATACTTGA (SEQ ID NO: 15) | m1 | m1 | | | m1 | | |
| m2 | 7 | TTTGCCA | m2 | m2 | m2 | m2 | | m2 | m2 |
| m3 | 13 | GAAATCTTCTCTC (SEQ ID NO: 16) | m3 | m3 | | | m3 | | |
| m4 | 17 | GATCTCACCTTCTCCTT (SEQ ID NO: 17) | m4 | m4 | | | m4 | | |
| m6 | 9 | GTAGCTTCA | m6 | | | | m6 | | |

TABLE 1-continued

| Motif ID | Motif length | Consensus | CYP704Bn-3 | CYP704Bn-5 | CYP704A1 | CYP704A2 | CYP704Bn-1 | CYP704Bn-2 | CYP704Bn-4 |
|---|---|---|---|---|---|---|---|---|---|
| m7 | 10 | TCATGATCCT (SEQ ID NO: 18) | m7 | m7 | | m7 | | | |
| m9 | 11 | TAATGAAGAAG (SEQ ID NO: 19) | m9 | m9 | | m9 | | | |
| m10 | 29 | TCATGTAAACCCCAC TCTTCTGCTCTAAC (SEQ ID NO: 20) | m10 | | | m10 | | | |
| m13 | 11 | TCCTCTTTCGC (SEQ ID NO: 21) | m13 | m13 | | m13 | | | |
| m14 | 17 | AAATCGAAGTATCCT TT (SEQ ID NO: 22) | m14 | m14 | | m14 | | | |
| m15 | 11 | AGCTTATACGC (SEQ ID NO: 23) | m15 | m15 | | m15 | | | |
| m16 | 9 | CGTTCGTTA | m16 | m16 | | m16 | | | |
| m17 | 8 | TAACCGGA | m17 | m17 | | m17 | | m17 | |
| m18 | 11 | CTCCATCGATA (SEQ ID NO: 24) | m18 | m18 | | m18 | | | |
| m19 | 8 | TTCATGGA | m19 | m19 | | m19 | m19 | | |
| m21 | 7 | TAGGATC | m21 | | | m21 | | m21 | |
| m22 | 9 | TTAGATTCT | m22 | m22 | | m22 | | | |
| m23 | 28 | GAGCTAAACGAATCA ATTATACCTCTGA (SEQ ID NO: 25) | | | | m23 | | | |
| m24 | 14 | GAAACTCATATCTA (SEQ ID NO: 26) | m24 | | | m24 | | | |
| m25 | 10 | AAAAAACAAA (SEQ ID NO: 27) | m25 | m25 | | m25 | | | |
| m26 | 18 | GGTTTCACGCACCAT GTT (SEQ ID NO: 28) | m26 | | | m26 | | | |
| m27 | 13 | AGAAAGAAGGTTC (SEQ ID NO: 29) | m27 | | | m27 | | | |
| m28 | 10 | TATACATATA (SEQ ID NO: 30) | m28 | | | m28 | | | |
| m29 | 10 | GATCATCTTC (SEQ ID NO: 31) | m29 | m29 | m29 | m29 | m29 | | m29 |

The table shows the presence of DOOP motifs on CYP704 promoter sequences. CYP704A1 (SEQ ID NO: 1) and CYP704A2 (SEQ ID NO: 2) are *A. thaliana* promoters. CYP704Bn-1, CYP704Bn-2, CYP704Bn-3, CYP704Bn-4 and CYP704Bn-5 are *B. napus* promoter sequences. The analysis shows that the CYP704Bn-3 and CYP704Bn-5 promoters of *B. napus* share a significant number of sequence consensus motifs with the CYP704A2 promoter from *A. thaliana*.

6. Vector Construction for Overexpression and Gene "Knockout" Experiments

Vectors used for expression of full-length "candidate nucleic adds" of interest in plants are designed to (over) express the protein of interest in a seed-preferred way and are of two general types, biolistic and binary, depending on the plant transformation method to be used. For biolistic transformation (with so called biolistic vectors), the requirements are as follows.

A backbone with a bacterial selectable marker (typically an antibiotic resistance gene) and origin of replication functional in *Escherichia coli* (e.g. ColEI), and (2) a plant-specific portion consisting of: a. a gene expression cassette consisting of the promoter depicted in SEQ ID NO: 1 SEQ ID NO: 2, SEQ ID NO: 13 or SEQ ID NO: 14 or a functional fragment of at least 50 consecutive bases of SEQ ID NO: 1, SEQ ID NO: 2, SEQ ID NO: 13 or SEQ ID NO: 14 or a nucleotide sequence having at least 40% identity with SEQ ID NO: 1, SEQ ID NO: 2, SEQ ID NO: 13 or SEQ ID NO: 14 or a functional fragment of at least 40% identity to a fragment of at least 50 consecutive bases of SEQ ID NO: 1, SEQ ID NO: 2, SEQ ID NO: 13 or SEQ ID NO: 14—the gene of interest (typically a full-length cDNA) and a transcriptional terminator (e.g. the *Agrobacterium tumefaciens* nos terminator); b. a pant selectable marker cassette, consisting of a suitable promoter, a selectable marker gene and transcriptional terminator (e.g. the nos terminator).

Vectors designed for transformation by *Agrobacterium tumefaciens* (so called binary vectors) consist of a backbone with a bacterial selectable marker functional in both *E. coli* and *A. tumefaciens* (e.g. spectinomycin resistance mediated by the aadA gene) and two origins of replication, functional in each of aforementioned bacterial hosts, pus the *A. tumefaciens* virG gene, (2) a plant-specific portion as described for biolistic vectors above, except in this instance this portion is flanked by *A. tumefaciens* right and left border sequences which mediate transfer of the DNA flanked by these two sequences to the plant.

Vectors designed for reducing or abolishing expression of a single gene or of a family or related genes (such as gene silencing vectors) specifically in seeds are also of two general types corresponding to the methodology used to downregulate gene expression: antisense or double-stranded RNA interference (dsRNAi). For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter whereby mRNA will be made from the non-coding (antisense) strand in a seed-preferred way in planta.

For dsRNAi vectors, a partial gene fragment is used in the gene expression cassette, and is expressed in both the sense and antisense orientations, separated by a spacer region (typically a plant intron or a selectable marker). Vectors of this type are designed to form a double-stranded mRNA stem, resulting from the base pairing of the two complementary gene fragments in a seed-preferred way in planta. Biolistic or binary vectors designed for overexpression or knockout can vary in a number of different ways, including e.g. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

7. Recombinant Expression of CYP704A2 in the Yeast *Saccharomyces cerevisiae*

The coding sequence of CYP704A2 (GenBank locus At2g45510, depicted in SEQ ID NO 3) was isolated by PCR carried out on *Arabidopsis thaliana* Col0 genomic DNA. After sequence verification, a cloning of this PCR-fragment was carried out into the *S. cerevisiae* expression vector pYeDP60. In the latter vector, SEQ ID No 3 is under transcriptional control of the inducible yeast chimeric GAL10-CYC1 hybrid promoter (Pompon, D et al (1996) Methods Enzymol 272: 51-64). The yeast strain WAT11 (Pompon, D et al (1996) as above) was subsequently transformed with this recombinant pYeDP60 vector. Expression of SEQ ID NO: 3 was induced by the addition of 2% galactose to the culture medium of a recombinant yeast comprising pYeDP60: CYP704A2 and after the induction phase microsomes were prepared according to Bak et al (2000) Plant Physiology 123(4):1437-48. The estimated expression of CYP704A2 was measured in a solution of microsomes and estimated at 0.13 nmol of cytochrome P450/mg microsomal protein.

8. Substrate Specificity of Recombinant CYP704A2

The enzyme activity and substrate specificity of CYP704A2 was subsequently evaluated. Thereto 20 µl of microsomal membranes overexpressing CYP704A2 (i.e. 80 nmoles of the enzyme) were incubated 20 min at 27° C. with 100 µM of different $^{14}$C radiolabelled fatty acids, alkanols or alkanes (purchased with American Radiolabeled Chemicals) together with 0.1 mM of NADPH, 0.4 Units of glucose-6-phosphate dehydrogenase, 3 mM glucose-6-phosphate in buffer NaPi 20 mM, pH 7.4 in a final reaction volume of 100 µl. The reaction was quenched by the addition of 20 µl of 20% of acetonitrile in water, and the incubation mix was spotted on silicagel 60F$_{254}$ plates (Merck) for analysis. Plates were developed with a mix of ether/petroleum ether/formic acid 50/50/1 until the migration front reached the top of the plate. Dried plates were then scanned with a Raytest radioisotope thin-layer analyzer and radioactivity in the spots of interest was quantified in order to evaluate the substrate conversion. Substrate specificity was evaluated with different fatty acids: capric acid (C10:0), lauric acid (C12:0), myristic acid (C14:0), palmitic acid (C16:0), stearic acid (C18:0), oleic acid (C18:1), linoleic acid (C18:2), linolenic acid (C18:3) (FIG. 5), the incubations products were analyzed by TLC. A single radioactive polar product was formed in the presence of NADPH, except for capric, myristic, palmitoleic and stearic acids which were not substrates. Comparison of the relative rates of metabolism of the different fatty acids indicated that palmitic acid was the best substrate (Table 2). The rate of palmitic acid metabolism was 18.3 nmol/min/nmole of P450 for a concentration of palmitic acid of 100 µM. Among C18 fatty acids, stearic acid was not metabolized, even after adding α-cyclodextrin at different concentrations to increase solubility, and oleic acid was more efficiently metabolized than linoleic acid. GC/MS analysis was carried out on a gas chromatograph (Agilent 6890 Series) equipped with a 30 cm capillary column with an internal diameter of 0.25 mm and a film thickness of 0.25 µm (HP-5MS). The gas chromatograph was combined with a quadrupole mass selective detector (Agilent 5973N). Mass spectra were recorded at 70 eV. GC/MS analysis was carried out to identify the oxygenated products after partial purification by scrapping the radiolabeled products of interest on the TLC plate. For GC-analysis the carboxyl groups were derivatized towards the methylic ester with the aid of diazomethane to make them more volatile. Hydroxylated groups of the fatty acids were modified with MSTFA (Thermo-scientific) before mass spectrometric analysis, MSTA adds a trimethylsilyl group on an existing hydroxyl-group and makes the derivatized fatty acid more "fragile" under mass spectrometric conditions. Methylation of the carboxylate group and silylation of the hydroxyl group were done by addition of 100 µl of freshly prepared diazomethane and MSTFA, respectively, and incubation for 30 min at room temperature. The reaction products for each fatty acid fragmented as an ω-hydroxy fatty acid. It was demonstrated that C16:0 was preferentially metabolized.

TABLE 2

Compared enzyme activity of CYP704A2 with fatty acids, alkanols and alkanes.

| | C12:0 | C12-OH:0 | C16:0 | C16-OH:0 | C16 alkane |
|---|---|---|---|---|---|
| % of metabolisation | 5.7 | 9.8 | 14.3 | 5.3 | 7.1 |
| Product (nmole/min/nmole P450) | 7.3 | 12.6 | 18.3 | 6.5 | 22.4 |

Microsomes prepared from yeast expressing CYP704A2 were incubated with 100 µM of radiolabeled substrates. Incubations were carried out for 20 min at 27° C. and contained 78 pmoles of CYP704A2. Activities were determined as described in 'Experimental procedures' by monitoring by TLC the formation of the metabolites.

9. CYP704A2 Catalyzes Hydroxylation of Alkanes and Fatty Alcohols (Alkanols)

A few P450 enzymes from microorganisms and animal source have been reported to ω-hydroxylate alkanes such as for example cytochromes P450 belonging to the CYP52 family isolated from fungi such as *Candida tropicalis* (Seghezzi W. et al. (1992) DNA Cell Biol. 11(10):767-780 and *C. maltosa* (Scheller U. et al. (1996) Arch. Biochem. Biophys. 328 (2):245-254, from bacteria such as P450 from *Rhodococcus rhodochrous* (Cardini G. and Jurtshuk P. (1970) J. Biol. Chem. 245:2789-2796) and CYP153 from *Acetinobacter calcoacetinus* EB104 (Funhoff E G et al. (2006) J. Bacteriol. 188:5220-5227), or also rabbit CYP4B1 (Fischer M B et al. (1998) Biochem. Biophys. Res. Commun. 248:352-355). C12 and C16 fatty alcohols and alkanes were tested as substrates of CYP704A2. Incubation of CYP704A2 with dodecanol leads to the formation of two more polar compounds. Their purification on TLC and subsequent analysis by GC/MS confirmed the hypothesis that one of the products was dodecanediol and the second product was ω-hydroxy lauric acid. To the best of our knowledge this is the first time that a plant P450 is capable of metabolizing a fatty alcohol (id est an alkanol).

Incubation of CYP704A2 with hexadecane lead to the formation of three more polar compounds. Their purification by TLC and subsequent analysis by GC/MS showed that one of them is hexadecanol, the second is hexadecane diol and the third is ω-hydroxy palmitic acid. The activity of CYP704A2 compares to the activities reported for the fungal enzymes (Scheller U et al. (1996) as above). Contrary to the fungal enzymes, it converts alkanes into alcohols, diols and hydroxy fatty acids, but not into dicarboxylic acids.

The invention claimed is:

1. An expression cassette for regulating seed-specific expression in plants comprising a promoter operably linked to a nucleic acid which is heterologous in relation to said promoter and wherein said promoter comprises the nucleotide sequence of SEQ ID NO: 13.

2. The expression cassette of claim 1 wherein the expression of the nucleic acid results in expression of a protein, or expression of an antisense RNA, sense or double-stranded RNA.

3. A recombinant vector comprising an expression cassette according to claim 1.

4. A transformed plant containing the expression cassette of claim 1.

5. The transformed plant of claim 4 wherein said transformed plant is a plant used for oil production.

6. The transformed plant according to claim 5 wherein the plant is selected from the group consisting of canola, maize, mustard, castor bean, sesame, cotton, linseed, soybean, *Arabidopsis, Phaseolus*, peanut, alfalfa, wheat, rice, oat, sorghum, rapeseed, rye, sugarcane, safflower, oil palms, flax, sunflower, *Brassica campestris, Brassica napus, Brassica juncea* and *Crambe abyssinica*.

7. A plant cell comprising an expression cassette of claim 1.

8. A microspore comprising an expression cassette of claim 1.

9. A seed generated from a transformed plant wherein the seed comprises an expression cassette according to claim 1.

10. A method of producing a transformed plant comprising (a) providing an expression cassette of claim 1 and (b) transforming a plant with said expression cassette.

11. A method of producing a seed comprising (a) growing a transformed plant containing the expression vector of claim 1, wherein said transformed plant produces said seed and said nucleic acid is transcribed in said seed, and (b) isolating said seed from said transformed plant.

* * * * *